(12) United States Patent
Akhtari et al.

(10) Patent No.: US 9,011,913 B2
(45) Date of Patent: *Apr. 21, 2015

(54) USE OF FUNCTIONALIZED MAGNETIC NANOPARTICLES IN CANCER DETECTION AND TREATMENT

(75) Inventors: Massoud Akhtari, Pasadena, CA (US); Jerome Engel, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 108 days.

This patent is subject to a terminal disclaimer.

(21) Appl. No.: 12/934,048

(22) PCT Filed: Apr. 1, 2009

(86) PCT No.: PCT/US2009/002061
§ 371 (c)(1), (2), (4) Date: Oct. 21, 2010

(87) PCT Pub. No.: WO2009/123735
PCT Pub. Date: Oct. 8, 2009

(65) Prior Publication Data
US 2011/0044911 A1    Feb. 24, 2011

Related U.S. Application Data

(60) Provisional application No. 61/042,654, filed on Apr. 4, 2008.

(51) Int. Cl.
| | | |
|---|---|---|
| A61K 9/14 | (2006.01) | |
| A61K 49/18 | (2006.01) | |
| A61K 41/00 | (2006.01) | |
| A61K 47/48 | (2006.01) | |
| B82Y 5/00 | (2011.01) | |

(52) U.S. Cl.
CPC .......... *A61K 49/1866* (2013.01); *A61K 41/0052* (2013.01); *A61K 47/48238* (2013.01); *A61K 47/48861* (2013.01); *A61K 49/1845* (2013.01); *A61K 49/1863* (2013.01); *B82Y 5/00* (2013.01)

(58) Field of Classification Search
CPC .......... A61K 9/5094; A61K 47/48861; A61K 41/00; A61K 47/4893; A61K 49/101
See application file for complete search history.

(56) References Cited

U.S. PATENT DOCUMENTS

| | | | |
|---|---|---|---|
| 5,132,111 A * | 7/1992 | Vale et al. ................... | 530/324 |
| 5,262,176 A | 11/1993 | Palmacci et al. | |
| 5,612,019 A | 3/1997 | Gordon et al. | |
| 5,622,686 A | 4/1997 | Gordon et al. | |
| 6,548,264 B1 | 4/2003 | Tan et al. | |
| 6,635,740 B1 * | 10/2003 | Enright et al. ................ | 530/324 |
| 6,767,635 B1 | 7/2004 | Bahr et al. | |
| 6,797,380 B2 | 9/2004 | Bonitatebus, Jr. et al. | |
| 2004/0146855 A1 | 7/2004 | Marchessault et al. | |
| 2005/0214221 A1 * | 9/2005 | Poss et al. ................... | 424/9.6 |
| 2005/0260137 A1 | 11/2005 | Acar et al. | |
| 2006/0142749 A1 * | 6/2006 | Ivkov ........................... | 606/27 |
| 2006/0171893 A1 * | 8/2006 | Zheng et al. ................. | 424/9.6 |
| 2007/0217998 A1 | 9/2007 | Wong | |
| 2007/0258889 A1 | 11/2007 | Douglas et al. | |
| 2007/0277649 A1 | 12/2007 | Xiao et al. | |
| 2007/0292353 A1 | 12/2007 | Levy et al. | |

FOREIGN PATENT DOCUMENTS

| | | |
|---|---|---|
| WO | WO 03/055379 | 10/2003 |
| WO | WO 2007021621 A2 * | 2/2007 |

OTHER PUBLICATIONS

Zwermann, O., et al., "ACTH 1-24 inhibits proliferation of adrenocortical tumors in vivo." 2005, European Journal of Endocrinology, 153, pp. 435-444.*
Berry et al., "Functionalisation of magnetic nanoparticles for applications in biomedicine" *J. Phys. D: Applied Physics*, (2003) 36:R198-R206.
Dousset et al., "Comparison of Ultra small Particles of Iron Oxide (USPIO)-Enhanced T2-Weighted,Conventional T2-Weighted,and Gadolinium-Enhanced T1-Weighted MR Images in Rats with Experimental Autoimmune Encephalomyelitis"*Am. J. Neuroradiol.*, (1999) 20:223-227.
Dousset et al., "In Vivo Macrophage Activity Imaging in the Central Nervous System Detected by Magnetic Resonance" *Magnetic Resonance in Medicine*, (1999) 41:329-333.
Dunning et al., "Superparamagnetic Iron Oxide-Labeled Schwann Cells and Olfactory Ensheathing Cells Can Be Traced InVivo by Magnetic Resonance Imaging and Retain Functional Properties after Transplantation into the CNS" *J. Neurosci.*, (2004) 24:9799-9810.
Moghimi et al., "Long-Circulating andTarget-Specific Nanoparticles:TheorytoPractice" *Pharmacol. Rev.*, (2001) 53:283-318.
Pankhurst et al., "Applications of Magnetic nanoparticles in Biomedicine" *J. Phys. D: Applied Physics*, (2003) 36:R167-R181.

* cited by examiner

*Primary Examiner* — Michael G Hartley
*Assistant Examiner* — Lance Rider
(74) *Attorney, Agent, or Firm* — Bozicevic, Field & Francis, LLP; Paula A. Borden

(57) ABSTRACT

The present invention provides methods of detecting a cancer cell in an individual, methods of grading a cancer, and methods of treating a cancer. The methods involve use of functionalized magnetic nanoparticles that comprise a moiety that provides for selective association with, and/or metabolic uptake into, a cancer cell.

21 Claims, 5 Drawing Sheets

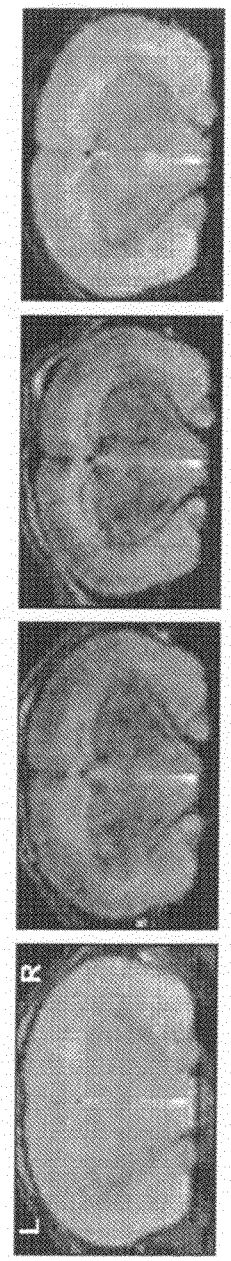

```
                        SEQUENCE LISTING

<160> NUMBER OF SEQ ID NOS: 6

<210> SEQ ID NO 1
<211> LENGTH: 28
<212> TYPE: PRT
<213> ORGANISM: Homo sapiens

<400> SEQUENCE: 1

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 2
<211> LENGTH: 14
<212> TYPE: PRT
<213> ORGANISM: Bombina bombina

<400> SEQUENCE: 2

Glu Gln Arg Leu Gly Asn Gln Trp Ala Val Gly His Leu Met
1               5                   10

<210> SEQ ID NO 3
<211> LENGTH: 14
<212> TYPE: PRT
<213> ORGANISM: Homo sapiens

<400> SEQUENCE: 3

Ala Gly Cys Lys Asn Phe Phe Trp Lys Thr Phe Thr Ser Cys
1               5                   10

<210> SEQ ID NO 4
<211> LENGTH: 39
<212> TYPE: PRT
<213> ORGANISM: Homo Sapiens

<400> SEQUENCE: 4

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
```

```
                    20                  25                  30

Glu Ala Phe Pro Leu Glu Phe
                35

<210> SEQ ID NO 5
<211> LENGTH: 41
<212> TYPE: PRT
<213> ORGANISM: Homo sapiens

<400> SEQUENCE: 5

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
                20                  25                  30

Ser Asn Arg Lys Leu Met Glu Ile Ile
                35                  40

<210> SEQ ID NO 6
<211> LENGTH: 38
<212> TYPE: PRT
<213> ORGANISM: Homo sapiens

<400> SEQUENCE: 6

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
                20                  25                  30

Gln Arg Val Lys Asn Lys
                35
```

USE OF FUNCTIONALIZED MAGNETIC NANOPARTICLES IN CANCER DETECTION AND TREATMENT

CROSS-REFERENCE

This application claims the benefit of U.S. Provisional Patent Application No. 61/042,654, filed Apr. 4, 2008, which application is incorporated herein by reference in its entirety.

BACKGROUND

Various imaging techniques are currently in use to diagnose, stage, and monitor tumors. Each technique currently in use has certain drawbacks. For example, many primary or metastatic tumors cannot be differentiated from normal tissues. Positron emission tomography (PET), PET-computed tomography (PET-CT), and single photon emission computed tomography (SPECT) are used routinely to look for tumor activity as well as grading of tumors. PET and SPECT involve administration of radioactive substances, have short half-life times, are not widely available, and are limited in their usefulness as diagnostic techniques.

There is a need in the art for imaging compositions and methods that avoid one or more of the above-mentioned drawbacks.

Literature

U.S. Pat. Nos. 6,548,264, 6,767,635; Berry and Curtis (2003) *J. Phys. D: Applied Physics* 36:R198-R206; Pankhurst et al. (2003) *J Phys. D: Applied Physics* 36:R167-R181; Dousset et al. (1999) *Am. J. Neuroradiol.* 20:223-227; Dunning et al. (2004) *J. Neurosci.* 24:9799-9810; Dousset et al. (1999) *Magnetic Resonance in Medicine* 41:329-333; Moghimi et al. (2001) *Pharmacol. Rev.* 53:283-318; U.S. Pat. No. 5,262,176; U.S. Pat. No. 6,797,380; US 2005/0260137; US 2007/0217998; US 2005/0214221; US 2004/0146855; WO 03/055379;U.S. Pat. No. 5,622,686; U.S. Pat. No. 5,612,019.

SUMMARY OF THE INVENTION

The present disclosure provides methods of detecting a cancer cell in an individual, methods of grading a cancer, and methods of treating a cancer. The methods involve use of functionalized magnetic nanoparticles that comprise a moiety that provides for selective association with, and/or metabolic uptake into, a cancer cell.

BRIEF DESCRIPTION OF THE DRAWINGS

FIGS. 2A-D depict 2DG-MNP contrast enhancement in a resting mouse brain.

DEFINITIONS

Figures 1A, 1B, 1C, 1D:
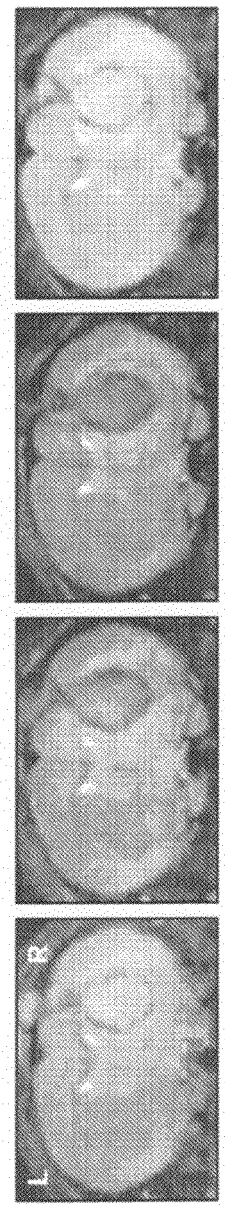
FIGS. 1A-D depict results of tumor studies with 2DG-MNP.

As used herein, the term "nanoparticle" refers to a particle having a diameter of between about 1 and 1000 nm. Similarly, by the term "nanoparticles" refers to a plurality of particles having an average diameter of between about 1 and 1000 nm.

Reference to the "size" of a nanoparticle is a reference to the length of the largest straight dimension of the nanoparticle. For example, the size of a perfectly spherical nanoparticle is its diameter.

As used herein, the term "functional group," used interchangeably with "functional moiety" and "functional ligand," refers to a chemical group that imparts a particular function to a magnetic nanoparticle bearing the chemical group. For example, functional groups can include macromolecular substances such as antibodies, oligonucleotides, carbohydrates, biotin, or streptavidin, polypeptides, polypeptides (including polypeptides that comprise non-amino acid moieties such as phosphate groups, sugars, carbohydrates, lipids, etc.), and hormones. Functional groups can include macromolecular substances that are known to bind particular molecules, where such macromolecular substances are members of specific binding pairs. Functional groups can include small chemical groups comprising moieties such as amines, amides, pyridinium, quinazolines, heterocyclic groups, aryl groups, carboxylates, and the like. Functional groups can comprises a radioactive moiety. For example, a functional group includes any of the foregoing groups, where the group is radioactive.

As used herein, the terms "subject," "individual," and "patient" refer interchangeably to any subject for whom or which diagnosis, prognosis, or therapy is desired, and generally refers to the recipient of a diagnostic method, a prognostic method, or a therapeutic method, to be practiced according to the invention. Suitable subjects include vertebrates, e.g., mammals. Suitable mammalian subjects include, but are not limited to, humans, non-human primates, rodents (e.g., rats, mice), ungulates (e.g., bovines, ovines, porcines, equines, etc.), felines, and canines.

As used herein, the terms "differential binding" or "selective binding," in the context of differential binding or selective binding of a functionalized MNP to a particular tissue, refer to binding of a functionalized MNP to a first tissue in such a manner that the binding to the first tissue is distinguishable from binding (if any) of the functionalized MNP to a second tissue. For example, in some embodiments, a subject functionalized MNP binds to a diseased tissue in such a manner that the binding of the functionalized MNP to the diseased tissue is distinguishable from binding (if any) of the functionalized MNP to a non-diseased tissue.

As used herein, the term "differential affinity" of a functionalized MNP for a particular tissue refers to binding of a functionalized MNP to the particular tissue with an affinity that is at least about 10%, at least 25%, at least about 50%, at least about 100% (or 2-fold), at least about 2.5-fold, at least about 5-fold, at least about 10-fold, at least about 50-fold, at least about $10^2$-fold, at least about $5\times10^2$-fold, at least about $10^3$-fold, at least about $5\times10^3$-fold, at least about $10^4$-fold, at least about $5\times10^4$-fold, at least about $10^5$-fold, or more, higher than the binding of the functionalized MNP to a second tissue. Differential affinity of a functionalized MNP can provide for differential binding or selective binding of the functionalized MNP to a particular tissue.

As used herein, the term "differential metabolic uptake" of a functionalized MNP into a particular tissue or cell refers to metabolic uptake of a functionalized MNP into a first tissue or a first cell in a manner that is distinguishable from the metabolic uptake of the functionalized MNP into a second tissue or a second cell. For example, in some embodiments, a functionalized MNP exhibits differential metabolic uptake into a diseased tissue in a manner that is distinguishable from the metabolic uptake (if any) of the functionalized MNP into a normal (non-diseased) tissue. As another example, in some embodiments, a functionalized MNP exhibits differential metabolic uptake into a cancer cell in a manner that is distinguishable from the metabolic uptake (if any) of the functionalized MNP into normal (non-cancerous) cell of the same cell type.

The terms "cancer," "neoplasm," and "tumor" are used interchangeably herein to refer to cells which exhibit relatively autonomous growth, so that they exhibit an aberrant growth phenotype characterized by a significant loss of control of cell proliferation. Cancerous cells can be benign or malignant.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, e.g., in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a functionalized magnetic nanoparticle" includes a plurality of such functionalized MNPs and reference to "the cancer cell" includes reference to one or more cancer cell and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of detecting a cancer cell in an individual, methods of grading a cancer, and methods of treating a cancer. The methods involve use of functionalized magnetic nanoparticles that comprise a moiety that provides for selective association with, and/or metabolic uptake into, a cancer cell.

Detection Methods

The present disclosure provides a method of detecting a cancer cell in an individual. The method generally involves: a) administering to an individual a composition comprising a functionalized magnetic nanoparticle (MNP), where the functionalized MNP comprises a functional moiety that provides for differential affinity for, and/or differential metabolic uptake into, a cancer cell, compared to a normal (non-cancerous) cell; and b) detecting the functionalized MNP in association with the cancer cell. The differential affinity for, and/ or differential metabolic uptake into, a cancer cell allows for discrimination between a cancerous tissue (e.g., a tissue comprising cancer cells) and non-cancerous tissues using available detection methods. The methods of the invention thus permit imaging of a cancerous tissue in a living subject. A subject detection method can be used to diagnose a cancer. A subject detection method permits detection of cancerous tissue, and also provides a way for medical personnel to monitor the progress of a patient undergoing treatment for the cancer. Thus, in some embodiments, a subject detection method is used to monitor patient response to treatment for the cancer, e.g., response to surgical removal of cancer, radiation treatment, bone marrow transplantation treatment, treatment with a cancer chemotherapeutic agent, etc.

A subject detection method allows imaging of a cancerous tissue in a living individual, e.g., a living mammal (e.g., a living rodent, a living human, a living non-human primate, a living ungulate, a living canine, a living feline, etc.). A subject method allows imaging of a cancerous tissue in a living individual without the need for radioactivity. Thus, in some embodiments, a functionalized MNP used in a subject method does not comprise any radioactive moieties. A functionalized MNP used in a subject method can include a radioactive moiety, but in many embodiments will not include any radioactive moiety.

In some embodiments, a functionalized MNP exhibits differential affinity for a particular cancerous mammalian tissue. In some embodiments, a functionalized MNP exhibits differential affinity for a cancerous mammalian tissue, e.g., a functionalized MNP exhibits an affinity for a cancerous tissue (e.g., a tissue that includes cancerous cells) that is at least about 10%, at least about 25%, at least about 50%, at least about 100% (or 2-fold), at least about 2.5-fold, at least about 5-fold, at least about 10-fold, at least about 15-fold, at least about 20-fold, at least about 50-fold, or at least about 100-fold, or more, higher than the affinity of the functionalized MNP for non-cancerous tissue of the same tissue type.

In some embodiments, a functionalized MNP exhibits differential metabolic uptake into a cancerous mammalian tissue such as a tumor, e.g., a functionalized MNP exhibits an at least about 1%, at least about 5%, at least about 10%, at least about 25%, at least about 50%, at least about 100% (or 2-fold), at least about 2.5-fold, at least about 5-fold, at least about 10-fold, at least about 15-fold, at least about 20-fold, at least about 50-fold, or at least about 100-fold, or more, greater metabolic uptake into the cancerous tissue (e.g., the tumor), compared to the metabolic uptake of the functionalized MNP into a non-cancerous tissue, e.g., a non-cancerous tissue of the same tissue type, or compared to the metabolic uptake of the functionalized MPN into normal, non-cancerous tissue adjacent to or surrounding a tumor. Whether a functionalized MNP exhibits differential metabolic uptake into a particular mammalian cell and/or tissue can be determined, e.g., using magnetic resonance imaging (MRI) or computed tomography (CT). A signal intensity change over time with repeated data acquisitions is observed when a functionalized MNP exhibits differential metabolic uptake into a cell and/or tissue.

In some embodiments, the detection step is carried out using an imaging method. In some embodiments, the imaging method is magnetic resonance imaging (MRI). In some embodiments, the imaging method is positron emission tomography (PET). In some embodiments, the imaging method is computed tomography (CT).

In some embodiments, a subject method provides for detection of a tumor, wherein a functionalized MNP exhibits differential affinity for the tumor, compared to the affinity of the functionalized MNP for a normal (non-cancerous) tissue. In some embodiments, a subject method provides for detection of a tumor, wherein a functionalized MNP exhibits differential metabolic uptake by the tumor, compared with the metabolic uptake of the functionalized MNP for normal (non-cancerous) tissue.

In some embodiments, a functionalized MNP provides for detection of a tumor that has a size (e.g., average diameter) of less than about 5 cm, less than about 2 cm, less than about 1.5 cm, less than about 1 cm, less than about 0.5 cm, less than about 250 mm, less than about 100 mm, less than about 50 mm, less than about 10 mm, less than about 1 mm, or less than about 0.5 mm. For example, a functionalized MNP provides for detection of a tumor that has a size (e.g., average diameter) of from about 0.5 mm to about 1 mm to about 5 mm, from about 5 mm to about 10 mm, from about 10 mm to about 25 mm, from about 25 mm to about 50 mm, from about 50 mm to about 100 mm, from about 100 mm to about 250 mm, from about 250 mm to about 500 mm, from about 500 mm to about 750 mm, from about 750 mm to about 1.0 cm, from about 1.0 cm to about 1.5 cm, from about 1.5 cm to about 2 cm, from about 2 cm to about 2.5 cm, from about 2.5 cm to about 3 cm, from about 3 cm to about 4 cm, or from about 4 cm to about 5 cm, or greater than 5 cm.

A subject method is useful for detecting a wide variety of neoplasms, including carcinomas, sarcomas, leukemias, and lymphomas. In some embodiments, the neoplasm is a solid tumor.

Carcinomas that can be detected using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma, etc.

Sarcomas that can be detected using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be detected using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be detected using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be detected using a subject method include, but are not limited to, B-cell lymphomas (e.g., Burkitt's lymphoma); Hodgkin's lymphoma; and the like.

Functionalized Magnetic Nanoparticles

Nanoparticles for use in a subject method generally have a mean size in a range of from about 1 nm to about 1500 nm, e.g., from about 1 nm to about 10 nm, from about 10 nm to about 50 nm, from about 50 nm to about 100 nm, from about 100 nm to about 250 nm, from about 250 nm to about 500 nm, from about 500 nm to about 750 nm, or from about 750 nm to about 1500 nm. Average diameters will in some embodiments range from about 10 nm to about 1500 nm, e.g., from about 10 nm to about 20 nm, from about 20 nm to about 40 nm, from about 40 nm to about 60 nm, from about 60 nm to about 80 nm, from about 80 nm to about 100 nm, from about 100 nm to about 200 nm, from about 200 nm to about 400 nm, from about 400 nm to about 600 nm, from about 600 nm to about 800 nm, from about 800 nm to about 1000 nm, or from about 1000 nm to about 1500 nm. This size refers to the magnetic core particle plus the coating (e.g., biocompatible substrate plus one or more functional moieties).

The magnetic core particle can have a diameter of from about 1 nm to about 1000 nm, e.g., from about 10 nm to about 20 nm, from about 20 nm to about 40 nm, from about 40 nm to about 60 nm, from about 60 nm to about 80 nm, from about 80 nm to about 100 nm, from about 100 nm to about 200 nm, from about 200 nm to about 400 nm, from about 400 nm to about 600 nm, from about 600 nm to about 800 nm, or from about 800 nm to about 1000 nm.

The coating can have a thickness (e.g., the average distance from the outside surface of the core magnetic particle to the outside surface of the coating) of from about 1 nm to about 500 nm, e.g., from about 1 nm to about 5 nm, from about 5 nm to about 10 nm, from about 10 nm to about 15 nm, from about 15 nm to about 20 nm, from about 20 nm to about 25 nm, from about 25 nm to about 30 nm, from about 30 nm to about 40 nm, from about 40 nm to about 50 nm, from about 50 nm to about 60 nm, from about 60 nm to about 70 nm, from about 70 nm to about 80 nm, from about 80 nm to about 90 nm, from about 90 nm to about 100 nm, from about 100 nm to about 125 nm, from about 125 nm to about 150 nm, from about 150 nm to about 175 nm, from about 175 nm to about 200 nm, from about 200 nm to about 225 nm, from about 225 nm to about 250 nm, from about 250 nm to about 275 nm, from about 275 nm to about 300 nm.

The ratio of the thickness of the coating to the diameter of the magnetic core particle is from about 1:1 to about 1:1000, e.g., from about 1:1 to about 1:1.5, from about 1:1.5 to about 1:2, from about 1:2 to about 1:2.5, from about 1:2.5 to about 1:5, from about 1:5 to about 1:10, from about 1:10 to about 1:25, from about 1:25 to about 1:50, from about 1:50 to about 1:100, from about 1:100 to about 1:250, from about 1:250 to about 1:500, from about 1:500 to about 1:750, or from about 1:750 to about 1:1000.

The diameter of the magnetic core of a functionalized MNP can be from about 1% to about 99% of the diameter of the entire functionalized MNP, e.g., the diameter of the magnetic core of a functionalized MNP can be from about 1% to about 5%, from about 5% to about 10%, from about 10% to about 25%, from about 25% to about 50%, from about 50% to about 75%, or from about 75% to about 99% of the diameter of the entire functionalized MNP.

The weight of the magnetic core of a functionalized MNP can be from about 1% to about 99% of the weight of the entire functionalized MNP, e.g., the weight of the magnetic core of a functionalized MNP can be from about 1% to about 5%, from about 5% to about 10%, from about 10% to about 25%, from about 25% to about 50%, from about 50% to about 75%, or from about 75% to about 99% of the weight of the entire functionalized MNP.

One or more properties of a functionalized MNP can vary, depending on the ratio of the diameter of the magnetic core to the diameter of the entire functionalized MNP. Such properties include, e.g., blood circulation time, resonance heating properties, transport across various tissues, transport across an endothelial cell layer, transport across the blood-brain barrier, particle clearance time, particle metabolism time, exposure of the core particle, MRI enhancement properties such as effect on T1, T2, T2*, effect on relaxation times of the particle in an externally applied magnetic field, and the like.

Nanoparticles can be simple aggregations of molecules or they can be structured into two or more layers of different substances. For example, simple nanoparticles consisting of magnetite or maghemite are suitable for use. See, e.g., Scientific and Clinical Applications of Magnetic Microspheres, U. Hafeli, W. Schutt, J. Teller, and M. Zborowski (eds.) Plenum Press, New York, 1997; and Tiefenauer et al., Bioconjugate Chem. 4:347, 1993. More complex nanoparticles can consist of a core made of one substance and one or more shells made of another substance(s). The term "magnetic nanoparticle" includes paramagnetic nanoparticles, diamagnetic nanoparticles, and ferromagnetic nanoparticles.

Exemplary core materials that are suitable for inclusion in a subject functionalized MNP include ferrites of general composition $MeO_xFe_2O_3$ where Me is a bivalent metal such as Co, Mn or Fe. Other suitable materials are $\gamma$-$Fe_2O_3$, the pure metals Co, Fe, Ni, and metal compounds such as carbides and nitrides. The core material is generally an MRI visible agent. The core material is typically coated. Suitable coatings include, but are not limited to, dextran, albumin, starch, silicon, and the like.

Many different type of small particles (nanoparticles or micron-sized particles) are commercially available from several different manufacturers including: Bangs Laboratories (Fishers, Ind.); Promega (Madison, Wis.); Dynal Inc. (Lake Success, N.Y.); Advanced Magnetics Inc. (Surrey, U.K.); CPG Inc. (Lincoln Park, N.J.); Cortex Biochem (San Leandro, Calif.); European Institute of Science (Lund, Sweden); Ferrofluidics Corp. (Nashua, N.H.); FeRx Inc.; (San Diego, Calif.); Immunicon Corp.; (Huntingdon Valley, Pa.); Magnetically Delivered Therapeutics Inc. (San Diego, Calif.); Miltenyi Biotec GmbH (USA); Microcaps GmbH (Rostock, Germany); PolyMicrospheres Inc. (Indianapolis, Ind.); Scigen Ltd. (Kent, U.K.); Seradyn Inc.; (Indianapolis, Ind.); and Spherotech Inc. (Libertyville, Ill.). Such particles can be made using conventional techniques, such as grinding and milling, emulsion polymerization, block copolymerization, and microemulsion.

Methods of making silica nanoparticles have also been reported. The processes involve crystallite core aggregation (Philipse et al., Langmuir, 10:92, 1994); fortification of superparamagnetic polymer nanoparticles with intercalated silica (Gruttner, C and J Teller, Journal of Magnetism and Magnetic Materials, 194:8, 1999); and microwave-mediated self-assembly (Correa-Duarte et al., Langmuir, 14:6430, 1998).

The core of a suitable functionalized MNP is magnetic and can include a metal selected from the group consisting of magnetite, maghemite, and greigite. Magnetic nanoparticles can be made using magnetic materials such as magnetite, maghemite, and greigite as part of the core. By varying the overall size and shape of such magnetic cores, they can be made superparamagnetic or stable single-domain (particles that retain a stable magnetic moment after being removed from a magnetic field). Core size relates to whether a magnetic nanoparticle is superparamagnetic or single-domain. Thus, relatively equidimensional superparamagnetic particles generally have a core sized less than 50 to 80 nm. At particle sizes above this upper range, the magnetization of the particle is split into domains of differing magnetization vectors in order to minimize internal magnetic energies.

In some embodiments, the core includes a pigment which can be an inorganic salt such as potassium permanganate, potassium dichromate, nickel sulfate, cobaltchloride, iron (III) chloride, or copper nitrate. Similarly, the core can include a dye such as Ru/Bpy, Eu/Bpy, or the like; or a metal such as Au, Ag, and Cd.

In some embodiments, the core includes a component selected from graphite, a graphite derivative, a carbon compound, a metal carbide, silicon carbide, and the like. For example, in some embodiments, the core includes maghemite, and a component selected from graphite, a graphite derivative, a carbon compound, a metal carbide, silicon carbide, and the like.

In some embodiments, a suitable functionalized nanoparticle comprises a core and a silica shell enveloping the core. The functional group is conjugated to the silica shell, e.g., as described in U.S. Pat. No. 6,548,264. Numerous known methods for attaching functional groups to silica can be adapted for use in a subject method. See, e.g., Ralph K. Iler, The Chemistry of Silica: Solubility, Polymerization, Colloid and Surface Properties, and Biochemistry, Wiley-Interscience, NY, 1979; VanDerVoort, P. and Vansant, E. F., Journal of Liquid Chromatography and Related Technologies, 19:2723-2752, 1996; and Immobilized Enzymes. Antigens, Antibodies, and Peptides: Preparation and Characterization, Howard H. Weetall (ed.), M. Dekker, NY, 1975. A typical process for adding functional groups to silica-coated nanoparticles involves treating the nanoparticles with a silanizing agent that reacts with and couples a chemical group to the silica surface of the nanoparticles. The chemical group can itself be the functional group, or it can serve as a substrate to which functional groups can be coupled.

For example, in an exemplary method, silica-coated nanoparticles are prepared as described above and the particle surfaces are silanized using trimethylsilylpropyl-diethylenetriamine (DETA), a silanization agent that attaches primary amine groups to silica surfaces. Antibodies or other proteins can then be covalently coupled to the silanized surface using the cyanogen bromide (CNBr) method. As one example, CNBr-mediated coupling can be achieved by suspending silica-coated nanoparticles previously silanized with DETA in a 2 M sodium carbonate buffer and ultrasonicating the mixture to create a particle suspension. A solution of CNBr (e.g., 2 g CNBr/1 ml acetonitirile) is then added to the particle suspension to activate the nano particles. After washing the nanoparticles with a neutral buffer (e.g., phosphate buffered saline, pH 8), an antibody solution is added to the activated nanoparticle suspension causing the antibodies to become bound to the nanoparticles. A glycine solution can also be added to the antibody-coated nanoparticles to block any remaining unreacted sites.

In some embodiments, the magnetic nanoparticle is dextran coated. Magnetic nanoparticles are made using any known process. For example, magnetic iron-dextran particles can be prepared by mixing 10 ml of 50% (w/w) aqueous Dextran T-40 (Pharmacia) with an equal volume of an aqueous solution containing 1.51 g $FeCl_3$-$6H_2O$ and 0.64 g $FeCl_2$-$4H_2O$. While stirring, the mixture is titrated to pH 10-11 by the drop-wise addition of 7.5% (v/v) $NH_4OH$ heated to 60-65° C. in a water bath for 15 minutes. Aggregates are then removed by 3 cycles of centrifugation in a low-speed clinical centrifuge at 600×g for 5 minutes. The ferromagnetic iron-dextran particles are separated from unbound dextran by gel filtration chromatography on Sephacryl-300. Five ml of the reaction mixture is then applied to a 2.5×33 cm column and eluted with 0.1 M sodium acetate and 0.15 M NaCl at pH 6.5. The purified ferromagnetic iron-dextran particles collected in the void volume will have a concentration of 7-10 mg/ml as determined by dry weight analysis. Molday and Mackenzie (1982) Journal of Immunological Methods 52:353-367. Also see (Xianqiao (2003) China Particuology Vol. 1, No. 2, 76-79).

In some embodiments, a suitable functionalized magnetic nanoparticle is of the formula: M-(L)-Z, the linkage sites between L and Z having covalently bound functional groups, wherein M represents the magnetic core particle, L represents an optional linker group, and Z represents a functional group.

In other embodiments, a suitable functionalized magnetic nanoparticle is of the formula: M-S-(L)-Z, the linkage sites between S and L and L and Z having covalently bound functional groups, wherein M represents the magnetic core particle, wherein S represents a biocompatible substrate fixed to M, wherein M represents the magnetic core particle, L represents an optional linker group, and Z represents a functional group. In some embodiments, a suitable functionalized magnetic nanoparticle is of the formula: M-(L)-Z, where M represents the magnetic core particle, where L represents an optional linker group, and where Z represents a functional group. In other embodiments, a suitable functionalized magnetic nanoparticle is of the formula: M-S-(L)-Z, where M represents the magnetic core particle, where S represents a biocompatible substrate surrounding M or attached to M, where L represents an optional linker group, and where Z represents a functional group. Functional groups include moieties that provide for binding to a specific tissue type or cell type; moieties that provide for crossing the blood-brain barrier (BBB); therapeutic agents; and the like.

In some embodiments, a suitable functionalized magnetic nanoparticle comprises two or more different functional groups attached to the same core particle or to the same biocompatible substrate surrounding or attached to the core particle. For example, in some embodiments, a suitable functionalized magnetic nanoparticle is of the formula M-(L)-$Z_1Z_2$, or M-S-(L)-$Z_1Z_2$, where $Z_1$ and $Z_2$ are different functional groups, where M is a magnetic core particle, and where L, if present, is a linker. In some embodiments, for example, $Z_1$ is a 2DG moiety and $Z_2$ is a therapeutic agent. In other embodiments, for example, $Z_1$ is a 2DG moiety, and $Z_2$ is a cell type-specific binding moiety. In other embodiments, for example, $Z_1$ is a 2DG moiety; and $Z_2$ is a moiety that provides for crossing the blood-brain barrier (BBB). In some embodiments, a suitable functionalized magnetic nanoparticle is of the formula M-S-(L)-$Z_1Z_2$, where M is a magnetic core particle, where the moieties $Z_1$ and $Z_2$ are each linked to the substrate (S), either directly or via a linker (L) (e.g., L, if present, is a linker). In some embodiments, a suitable functionalized magnetic nanoparticle comprises at least a third functional moiety $Z_3$. Thus, e.g., in some embodiments, a suitable functionalized magnetic nanoparticle is of the formula M-S-(L)-$Z_1Z_2Z_3$, where the moieties $Z_1$, $Z_2$, and $Z_3$ are each linked to the substrate, either directly or via a linker. In some embodiments, $Z_1$ is a 2DG moiety; $Z_2$ is a first therapeutic agent; and $Z_3$ is a second therapeutic agent. In other embodiments, $Z_1$ is a 2DG moiety; $Z_2$ is a therapeutic agent; and $Z_3$ is a moiety that provides for crossing the BBB.

In some embodiments, the magnetic core particles consist of magnetite, maghemite, ferrites of general formula $MeO_xFe_2O_3$ wherein Me is a bivalent metal such as cobalt, gold, manganese, iron, or of cobalt, iron, nickel, iron carbide, or iron nitride, as described above. If present, the substrate S is a biocompatible substrate comprising one or more compounds such as polysaccharides or oligosaccharides or derivatives thereof, such as dextran, carboxymethyldextran, starch, dialdehyde starch, chitin, alginate, cellulose, carboxymethylcellulose; proteins or derivatives thereof, such as albumins, peptides, synthetic polypeptides, and polypeptides modified with a non-amino acid group such as a sugar, a lipid, a polysaccharide, a phosphate group, etc.; synthetic polymers, such as polyethyleneglycols, polyvinylpyrrolidone, polyethyleneimine, polymethacrylates, bifunctional carboxylic acids and derivatives thereof, such as mercaptosuccinic acid or hydroxycarboxylic acids; and radioactive versions of any of the foregoing.

The linker group L, if present, can be formed by reaction of a compound such as poly- and dicarboxylic acids, polyhydroxycarboxylic acids, diamines, amino acids, peptides, proteins, lipids, lipoproteins, glycoproteins, lectins, oligosaccharides, polysaccharides, oligonucleotides and alkylated derivatives thereof, and nucleic acids (DNA, RNA, PNA) and alkylated derivatives thereof, present either in single-stranded or double-stranded form, which compound includes at least two identical or different functional groups; or radioactive versions of any of the foregoing.

In some embodiments, a suitable functionalized magnetic nanoparticle is capable of passing the blood-brain barrier. For example, a functionalized magnetic nanoparticle may comprise, attached to the nanoparticle, or in a formulation with the nanoparticle, or coating the nanoparticle, one or more polymers. Suitable polymers that facilitate crossing of the blood brain barrier include, but are not limited to, surfactants such as polysorbate (e.g., Tween® 20, 40, 60 and 80); poloxamers such as Pluronic® F 68; and the like. In some embodiments, a subject functionalized magnetic nanoparticle is coated with a polysorbate such as, e.g., Tween® 80 (which is Polyoxyethylene-80-sorbitan monooleate), Tween® 40 (which is Polyoxyethylene sorbitan monopalmitate); Tween® 60 (which is Polyoxyethylene sorbitan monostearate); Tween® 20 (which is Polyoxyethylene-20-sorbitan monolaurate); polyoxyethylene 20 sorbitan monopalmitate; polyoxyethylene 20 sorbitan monostearate; polyoxyethylene 20 sorbitan monooleate; etc. Also suitable for use are water soluble polymers, including, e.g.: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); dextran, and proteins such as albumin. Block co-polymers are suitable for use, e.g., a polyethylene oxide-polypropylene oxide-polyethylene-oxide (PEO-PPO-PEO) triblock co-polymer (e.g., Pluronic® F68); and the like; see, e.g., U.S. Pat. No. 6,923,986. Other methods for crossing the blood brain barrier are discussed in various publications, including, e.g., Chen et al. (2004) Curr. Drug Delivery 1:361-376.

In some embodiments, a suitable functionalized MNP comprises one or more agents that provide for evasion of the reticuloendothelial system (RES). Agents that provide for evasion of the RES include, but are not limited to, a block copolymer non-ionic surfactant such as a poloxamine, such as poloxamine 508, poloxamine 908, poloxamine 1508, etc. In some embodiments, a subject functionalized MNP comprises about 1% poloxamine.

Nanoparticles can also be transferred across the BBB by utilizing the specific delivery channels that are present in the BBB. As one non-limiting example, attachment of alpha-methyl tryptophan to the nanoparticles renders the tryptophan channels receptive to these particles and aids in delivery across the BBB. Other mechanisms are transcytosis and diapedesis, with or without the mediation of the channels present at the BBB.

Functional Moieties

As noted above, a functionalized MNP suitable for use in a subject method comprises at least one functional moiety ("functional group"), where the at least one functional moiety provides for differential affinity for, and/or differential metabolic uptake into, a cancer cell, compared to a normal (non-cancerous) cell, e.g., compared to a normal (non-cancerous) cell of the same tissue type or cell type.

Suitable functional moieties that provide for differential affinity for, and/or differential metabolic uptake into, a cancer cell include, but are not limited to, 2-deoxyglucose (2DG); an amino acid; thymidine; choline; methylcholine; fluoride; an androgen receptor ligand; an estrogen receptor ligand; an antineoplastic agent; a vasoactive intestinal peptide receptor ligand; 1,4,7-triazacyclononane-1,4,7-triyltriacetic acid (NOTA); 1,4,7,10-tetraazacyclododecane-1,4,7,10-tetrayltetra-acetic acid (DOTA); diethylenenetriaminepentaacetic acid (DTPA); a gastrin releasing peptide receptor agonist; a gastrin releasing peptide receptor antagonist; a somatostatin receptor agonist; a somatostatin receptor antagonist; ACTH, CRF; benzoxazole; a benzoxazole derivative; taxane or a taxane derivative; a polyamine; cyclophosphamide; an Arginine-Glycine-Aspartic acid (RGD)-containing peptide; and a nucleotide analog.

In some embodiments, the functional group (moiety) is a vasoactive intestinal peptide receptor ligand. Vasoactive intestinal peptide (VIP) receptor ligands include VIP. VIP amino acid sequences are known in the art, and include, e.g., the amino acid sequences set forth in GenBank Accession Nos. CAI21764, CAI21765, CAI21766, AAA63268. Variants and fragments of any known VIP that have the ability to bind a VIP receptor on a cancer cell are also suitable as functional moieties. A VIP can have a length of 28 amino acids. Amino acid sequences of 28-amino acid VIP of various species are provided in FIG. 1 of WO 96/034958, the disclosure of which is incorporated by reference herein. For example, a 28-amino acid human VIP can have the amino acid sequence HSDAVFMNYTRLRKQMAVKKYLNSILN (SEQ ID NO:1). Those skilled in the art, given the disclosure in the art regarding various biologically active variants of VIP, can readily envision changes that can be made to the 28-amino acid sequence of human VIP, where such changes do not substantially affect the ability of the VIP to bind to a VIP receptor on a cancer cell. In some embodiments, VIP receptors are present on lung cancer cells (e.g., non-small cell lung carcinoma), and a subject method is useful for detecting a lung cancer cell in an individual. In some embodiments, VIP receptors are present on breast cancer cells, and a subject method is useful for detecting a breast cancer cell in an individual. In some embodiments, VIP receptors are present on gastrointestinal tumors, and a subject method is useful for detecting a gastrointestinal tumor in an individual. Gastrointestinal tumors include, e.g., colorectal cancer, pancreatic carcinoma, gastric cancer, carcinoid tumor, and insulinoma. In some embodiments, VIP receptors are present on prostate cancer cells, and a subject method is useful for detecting a prostate cancer cell in an individual, where a VIP-MNP conjugate is used.

In some embodiments, the functional moiety is 2-deoxyglucose (2DG), or a derivative or a variant of 2DG. As used herein, "2DG" includes 2DG derivatives and 2DG variants. 2-Deoxyglucose (2-DG) is also called 2-deoxy-D-glucose, 2-deoxy-D-arabino-hexose, or D-arabino-2-deoxyhexose. 2DG is a component of anticancer drugs such as daunomycin, adriamycin, caminomycins, and antibiotics with a lactonic ring. 2DG derivatives and variants include, but are not limited to, all therapeutic or functional molecules that contain one or more 2DG molecule(s) its derivatives or variants as part of their basic chemical structure. In some embodiments, a functionalized MNP that comprises 2DG as the functional moiety has differential affinity for, and/or differential metabolic uptake into, a cancer cell (e.g., a tumor).

In some embodiments, the 2DG is linked to the biocompatible substrate of the MNP via the oxygen atom of a hydroxyl group on the 2DG. Thus, e.g., in some embodiments, the 2DG is linked to the biocompatible substrate, directly or via a linker, via the 1-OH, the 3-OH, the 4-OH, or the 6-OH oxygen of the 2DG. In some embodiments, the 2DG is linked to the biocompatible substrate, directly or via a linker, via the 1-OH oxygen of the 2DG. In some embodiments, the 2DG is linked to the biocompatible substrate, directly or via a linker, via the 3-OH oxygen of the 2DG. In some embodiments, the 2DG is linked to the biocompatible substrate, directly or via a linker, via the 4-OH oxygen of the 2DG. In some embodiments, the 2DG is linked to the biocompatible substrate, directly or via a linker, via the 6-OH oxygen of the 2DG.

In other embodiments, the 2DG is linked to the biocompatible substrate of the MNP via a carbon atom of the 2DG. Thus, e.g., in some embodiments, the 2DG is linked, directly or via a linker, to the biocompatible substrate, via one of $C_{1-6}$ of the 2DG. In some embodiments, the 2DG is linked, directly or via a linker, to the biocompatible substrate, via $C_1$ of the 2DG. In some embodiments, the 2DG is linked, directly or via a linker, to the biocompatible substrate, via $C_2$ of the 2DG. In some embodiments, the 2DG is linked, directly or via a linker, to the biocompatible substrate, via $C_3$ of the 2DG. In some embodiments, the 2DG is linked, directly or via a linker, to the biocompatible substrate, via $C_4$ of the 2DG. In some embodiments, the 2DG is linked, directly or via a linker, to the biocompatible substrate, via $C_5$ of the 2DG. In some embodiments, the 2DG is linked, directly or via a linker, to the biocompatible substrate, via $C_6$ of the 2DG.

In some embodiments, the functional group is an androgen receptor ligand. Androgen receptor ligands include, but are not limited to, dihydrotestosterone; esters of testosterone, such as the cypionate, propionate, phenylpropionate, cyclopentylpropionate, isocarporate, enanthate, and decanoate esters; synthetic androgens such as 7-Methyl-Nortestosterone ("MENT") and its acetate ester; an androgen receptor ligand as described in U.S. Pat. No. 7,344,700; nandrolane decanoate, methyltestosterone, methanadrostenolone, stanozolol, fluoxymesterone, oxymetholone, oxandrolone, oxymethol, norethandrolone, ethylestranol, 4-androsten-19-a1-3,17-dione, 19-nortestosterone, norethandrone, norethisterone, dehydroepiandrosterone, epiandrosterone sulfate, androstenedione and androstenediol, testosterone propionate, testosterone cytpionate, and testosterone enanthate.

In some embodiments, the functional group is an estrogen receptor ligand. Estrogen receptor ligands include, but are not limited to, estrogen, norgestimate (NGM), ethinyl estradiol (EE), and 17-βestradiol ($E_2$), cyclofenil (bis(p-acetoxy phenyl)cyclohexylidene methane), 2-methoxyestrone, 6α-Hydroxyestradiol, 6-Dehydroestrone, 4-Hydroxyestrone, 2-Hydroxyestriol, 2-Hydroxyestradiol, 17α-Ethynylestradiol, 17α-Ethynylestradiol 3-cyclopentyl ether, 17-Epiestriol, 16-Epiestriol, and the like.

In some embodiments, the functional group is an RGD-containing peptide. RGD-containing peptides include peptides having a length of from about 7 amino acids to about 50 amino acids, and including an Arg-Gly-Asp (RGD) sequence. The RGD sequence can be at the carboxyl terminus, at the amino terminus, or at an internal site in the peptide. The RGD-containing peptide can be linear or cyclic. RGD-containing peptide can include a poly(ethylene glycol) moiety.

In some embodiments, the functional group is a gastrin releasing peptide receptor agonist. Gastrin releasing peptide receptor agonists include, but are not limited to, bombesin, a bombesin analog, a bombesin derivative, and a gastrin releasing peptide (GRP). Bombesin is a 14-amino acid peptide of the sequence: Glu-Gln-Arg-Leu-Gly-Asn-Gln-Trp-Ala-Val-Gly-His-Leu-Met (SEQ ID NO:2). Bombesin (BBN) analogs include, e.g., peptides having amino acid substitutions in the BBN (8-14) binding region (D-Ala$^{11}$ for L-Gly$^{11}$ or D-Trp$^8$ for L-Trp$^8$), which can be made without substantially decreasing binding affinity. Analogues of GRP include peptidomimetics or pseudopeptides incorporating changes to the amide bonds of the, peptide backbone, including thioamides, methylene amines, and E-olefins. Also suitable are peptides based on the structure of GRP, BBN or their peptide analogues with amino acids replaced by N-substituted hydrazine carbonyl compounds (also known as aza amino acids).

In some embodiments, the functional group is a gastrin releasing peptide receptor antagonist. Gastrin releasing peptide receptor antagonists include, but are not limited to, RC-3095 ((DTpi6, Leu3, psi[CH$_2$NH]-Leu14) bombesin (6 14)); BBN analogs having D-Pro-(CH$_2$NH)-Phe-NH$_2$ at the C-terminus (Leban et al. (1993) *Proc. Natl. Acad. Sci. USA* 90:1922); ψ 13,14 bombesin analogs; RC-3940-II; and the like. Also suitable for use is a bombesin antagonist as described in U.S. Pat. No. 6,989,371, e.g., a bombesin antagonist of the formula: X-D-Phe-Gln-R1-R2-Val-R3-His-R4-NH$_2$, where X is acetyl or straight, branched, or cyclic alkanoyl group from 3 16 carbon atoms, or X is deleted, where R1 is Trp or D-Trp, where R2 is Ala, Aib or Deg, where R3 is Gly, Aib, Deg, Dpg or Ac5c, where R4 is Leu or Ile or a hydrolyzable carboxy protecting group, where "Aib" is α-aminoisobutyric acid, Deg is α,α-diethyl glycine, Dpg is α,α-di-n-propyl glycine and Ac5c is 1-amino-cyclo pentane carboxylic acid. For example, a bombesin antagonist can comprise the amino acid sequence of any one of SEQ ID NOs:3-12 of U.S. Pat. No. 6,989,371.

A variety of BBN analogs are described in U.S. Pat. No. 5,834,433, U.S. Pat. No. 5,723,578, U.S. Pat. No. 5,620,959, U.S. Pat. No. 5,620,959, U.S. Pat. No. 5,428,019, U.S. Pat. No. 5,399,094, U.S. Pat. No. 5,084,555, and U.S. Pat. No. 6,200,546. Any known bombesin analog can be used as a functional moiety.

In some embodiments, the functional group is a somatostatin receptor ligand. Somatostatin receptor ligands include, e.g., somatostatin (e.g., a peptide having the amino acid sequence AGCKNFFWKTFTSC; SEQ ID NO:3); octreotide (L-Cysteinamide, D-phenylalanyl-L-cysteinyl-L-phenylalanyl-D-tryptophyl-L-lysyl-L-threonyl-N-[2-hydroxy-1-(hydroxymethyl)propyl]-, cyclic (2-7)-disulfide); lanreotide; vapreotide; a somatostatin analog as described in U.S. Pat. No. 6,552,007, U.S. Pat. No. 6,358,491, or U.S. Pat. No. 7,019,109; a non-peptide somatostatin receptor ligand as described in U.S. Pat. No. 7,189,856; and the like.

In some embodiments, the functional moiety is an adrenocorticotropin hormone (ACTH) polypeptide. A suitable ACTH polypeptide can comprise an amino acid sequence having at least about 75%, at least about 80%, at least about 85%, at least about 90%, at least about 95%, at least about 98%, at least about 99%, or 100%, amino acid sequence identity to a contiguous stretch of from 30 amino acids to 39 amino acids of the following sequence: sysmehfrwg kpvgkkrrpv kvypngaede saeafplef (SEQ ID NO:4). A suitable ACTH polypeptide binds an ACTH receptor on cell in a target tissue. A suitable ACTH polypeptide is a variant ACTH polypeptide that comprises one or more amino acid substitutions compared to the amino acid sequence set forth in SEQ ID NO:4, where the variant binds an ACTH receptor. For example, in some embodiments, a suitable ACTH polypeptide will have a Val instead of Leu at position 37 of SEQ ID NO:4. As another example, in some embodiments, a suitable ACTH polypeptide will have an Asp instead of a Glu at position 38 of SEQ ID NO:4. As another example, in some embodiments, a suitable ACTH polypeptide will have a Gln instead of a Glu at position 33 of SEQ ID NO:4. A suitable ACTH polypeptide can include heterologous amino acids, e.g., amino acids not normally associated with ACTH. In some embodiments, the ACTH polypeptide has a length of from about 30 amino acids to about 40 amino acids, from about 40 amino acids to about 50 amino acids, or from about 50 amino acids to about 100 amino acids. In some embodiments, a subject functionalized MNP that comprises ACTH as a functional group exhibits differential binding to adrenal dysplasia or to an adrenal tumor.

In some embodiments, the functional moiety is a corticotropin releasing factor (CRF) polypeptide. A suitable CRF polypeptide can comprise an amino acid sequence having at least about 75%, at least about 80%, at least about 85%, at least about 90%, at least about 95%, at least about 98%, at least about 99%, or 100%, amino acid sequence identity to a contiguous stretch of from 30 amino acids to 41 amino acids of the following sequence: seeppisldl tfhllrevle maraeqlaqq ahsnrklmei i (SEQ ID NO:5). A suitable CRF polypeptide binds a CRF receptor on cell in a target tissue. A suitable CRF polypeptide is a variant CRF polypeptide that comprises one or more amino acid substitutions compared to the amino acid sequence set forth in SEQ ID NO:5, where the variant binds a CRF receptor. For example, in some embodiments, a suitable CRF polypeptide will have an Ala instead of Ser at position 1 of the amino acid sequence set forth in SEQ ID NO:5. As another example, in some embodiments, a suitable CRF polypeptide will have an Ile instead of Leu at position 27 of the amino acid sequence set forth in SEQ ID NO:5. As another example, in some embodiments, a suitable CRF polypeptide will have an Asp instead of Glu at position 39 of the amino acid sequence set forth in SEQ ID NO:5. A suitable CRF polypeptide can include heterologous amino acids, e.g., amino acids not normally associated with CRF. In some embodiments, the CRF polypeptide has a length of from about 30 amino acids to about 40 amino acids, from about 40 amino acids to about 50 amino acids, or from about 50 amino acids to about 100 amino acids. In some embodiments, a functionalized MNP that comprises CRF as a functional group exhibits differential binding to a pituitary tumor.

In some embodiments, the functional moiety is a pituitary adenylyl cyclase activating polypeptide (PACAP) polypeptide. PACAP polypeptides include a polypeptide comprising an amino acid sequence having at least about 75%, at least about 80%, at least about 85%, at least about 90%, at least about 95%, at least about 98%, at least about 99%, or 100%, amino acid sequence identity to a contiguous stretch of from about 25 amino acids to about 30 amino acids, from about 30 amino acids to about 35 amino acids, or from about 35 amino acids to about 38 amino acids of the following sequence hsdgiftdsy sryrkqmavk kylaavlgkr ykqrvknk (SEQ ID NO:6). Also included are amidated variants of PACAP. Also included are N-terminal amidated 27-residue derivative of a PACAP polypeptide (e.g., amino acids 1-27 of the sequence set forth in SEQ ID NO:6); and any of the analogs and variants disclosed in, e.g., U.S. Pat. Nos. 5,128,242; 5,198,542; 5,208,320; 5,326,860; 5,623,050; 5,801,147 and 6,242,563. In some embodiments, a PACAP polypeptide is biologically active. In some embodiments, a PACAP polypeptide binds a mammalian (e.g., a human) PACAP receptor (see, e.g., GenBank BAA04466; and Ogi et al. (1993) *Biochem. Biophys. Res. Comm.* 196:1511). Also included are functional agonists of a PACAP receptor, e.g., maxadilan, a polypeptide that acts as a specific agonist of mammalian PACAP receptors. See, e.g., GenBank Accession No. AAA29288 for amino acid sequences of maxadilan. In some embodiments, a functionalized MNP that comprises a PACAP polypeptide exhibits differential binding to a pituitary tumor.

In some embodiments, the functional group is a taxane. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Additional Functional Moieties

As noted above, in some embodiments, a functionalized MNP comprises, in addition to a functional moiety (a "first functional moiety") that provides for differential affinity for and/or differential metabolic uptake into a cancer cell, at least a second functional moiety. In some embodiments, the at least a second functional moiety is a cancer chemotherapeutic agent. Cancer chemotherapeutic agents are non-peptidic (i.e., non-proteinaceous) compounds that reduce proliferation of cancer cells, and encompass cytotoxic agents and cytostatic agents.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and progestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283, 253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use in connection with the methods of the invention include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-alpha (IFN-α); (7) interferon-gamma (IFN-γ); (8) colony-stimulating factors; and (9) inhibitors of angiogenesis.

Detection

In carrying out a subject detection method (e.g., a cancer diagnostic method, a cancer monitoring method, a treatment efficacy monitoring method, as described below), a composition comprising a functionalized MNP is in some embodiments administered to an individual via a parenteral route of administration, e.g., intravenous, intramuscular, subcutaneous, intratumoral, intracranial, peritumoral, inhalational, ocular, topical, via the genito-urinary tract, etc. In carrying out a subject detection method (e.g., a cancer diagnostic method, a cancer monitoring method, a treatment efficacy monitoring method, as described below), a composition comprising a functionalized MNP is in some embodiments administered to an individual via an enteral route of administration, e.g., via an oral route of administration, via a gastrointestinal route of administration, or via rectal administration.

A suitable number of functionalized MNP are administered to an individual, where a suitable number ranges from about $10^2$ functionalized MNP to about $10^{19}$ functionalized MNP, e.g., from about $10^2$ to about $10^3$ functionalized MNP, from about $10^3$ to about $10^4$ functionalized MNP, from about $10^4$ to about $10^5$ functionalized MNP, from about $10^5$ to about $10^6$ functionalized MNP, from about $10^6$ to about $10^2$ functionalized MNP, from about $10^2$ to about $10^9$ functionalized MNP, from about $10^8$ to about $10^9$ functionalized MNP, from about $10^9$ functionalized MNP to about $10^{10}$ functionalized MNP, from about $10^{10}$ functionalized MNP to about $10^{12}$ functionalized MNP, from about $10^{12}$ functionalized MNP to about $10^{14}$ functionalized MNP, from about $10^{14}$ functionalized MNP to about $10^{16}$ functionalized MNP, or from about $10^{16}$ functionalized MNP to about $10^{18}$ functionalized MNP.

Cancer Diagnosis

In some embodiments, a subject detection method provides for diagnosis of cancer in an individual. The method generally involves administering to an individual (a living subject) an effective amount of a functionalized MNP that comprises a functional moiety that has differential affinity for and/or metabolic uptake into a cancer cell; and detecting association of the functionalized MNP with a cancer cell and/or a tissue comprising a cancer cell. The functionalized MNP selectively associates with a cancer cell in the subject. Detection can be carried out using any of a variety of known methods, including MRI, CT, and PET.

Where association of the functionalized MNP with a cancer cell and/or a tissue comprising a cancer cell is detected at a level that is above a background level in the individual, a diagnosis of cancer may be made.

In some embodiments, the nature of the functional moiety component of the functionalized MNP will provide an indication as to the type of cancer. For example, where the functionalized moiety is an estrogen receptor ligand, a diagnosis of breast cancer may be made, where association of the functionalized MNP with a cancer cell (e.g., a breast cancer cell) and/or a tissue (e.g., a breast tissue) comprising a cancer cell is detected at a level that is above a background level in the individual.

Where a subject detection method detects the presence of a cancerous or cell in an individual, in some embodiments the individual will undergo one or more confirmatory tests for the cancer. Where a subject detection method detects the presence of a cancerous cell in an individual, in some embodiments the individual will be treated for the cancer. Standard treatments can include, e.g., surgery (e.g., surgical removal of a tumor); radiation treatment; bone marrow transplantation; and chemotherapy.

A subject detection method can also be performed to monitor progression of a cancer. For example, a subject detection method can be performed on an individual once per week, once per month, bi-monthly, once every three months, once every four months, once every 6 months, or once a year, depending on various factors.

In some embodiments, the outcome of a subject diagnostic method is provided in a report. Thus, in some embodiments, a subject method further includes a step of preparing or generating a report that includes information regarding the results of the imaging method (e.g., detecting step). For example, a subject method can further include a step of generating or outputting a report providing the results of the imaging method (e.g., whether an individual has a tumor, size of the tumor, location of the tumor, etc.), which report can be provided in the form of an electronic medium (e.g., an electronic display on a computer monitor), or in the form of a tangible medium (e.g., a report printed on paper or other tangible medium).

In some embodiments, a subject detection method provides for detection of a tumor that has a size (e.g., average diameter) of less than about 5 cm, less than about 2 cm, less than about 1.5 cm, less than about 1 cm, less than about 0.5 cm, less than about 250 mm, less than about 100 mm, less than about 50 mm, less than about 10 mm, less than about 1 mm, or less than about 0.5 mm. For example, a subject detection method provides for detection of a tumor that has a size (e.g., average diameter) of from about 0.5 mm to about 1 mm to about 5 mm, from about 5 mm to about 10 mm, from about 10 mm to about 25 mm, from about 25 mm to about 50 mm, from about 50 mm to about 100 mm, from about 100 mm to about 250 mm, from about 250 mm to about 500 mm, from about 500 mm to about 750 mm, from about 750 mm to about 1.0 cm, from about 1.0 cm to about 1.5 cm, from about 1.5 cm to about 2 cm, from about 2 cm to about 2.5 cm, from about 2.5 cm to about 3 cm, from about 3 cm to about 4 cm, or from about 4 cm to about 5 cm, or greater than 5 cm.

Assessing Efficacy of Treatment for Cancer

Detection methods can also be performed to assess response to therapy for a cancer. For example, a subject detection method can be carried out on an individual to determine whether the individual is responding to treatment for a cancer. In some embodiments, a subject detection method is carried out before and after a treatment, e.g. surgery or a drug treatment, to determine if the treatment is efficacious. In other embodiments, a subject detection method is carried out on an individual during and/or after a course of the treatment, to determine whether the treatment slows the progression of the cancer, and to what extent the treatment slows the progression of the cancer. For example, a reduction of at least about 10%, at least about 20%, at least about 25%, at least about 30%, or at least about 40%, or more, in the size of a tumor in response to a given treatment indicates that the treatment is efficacious in treating the tumor. As another example, stabilization of the size of the tumor can indicate efficacy of treatment.

In some embodiments, a subject method involves: a) administering to an individual who has undergone a first treatment regimen for cancer a composition comprising a functionalized MNP; b) imaging a tissue or tissues in the individual to which the functionalized MNP is bound; and c) recommending a treatment. The imaging step (b) provides an indication as to whether the first treatment regimen is efficacious in treating the cancer. The imaging data are analyzed to determine whether the first treatment regimen was efficacious. For example, depending on whether the first treatment regimen is determined to be efficacious, a treatment regimen is recommended, which is the same or different from the first treatment regimen. If the first treatment regimen is deemed to be efficacious, it may be recommended to continue with the first treatment regimen (e.g., repeat the first treatment regimen), to carry out a second treatment regimen wherein an agent that is administered as part of the first treatment regimen is administered at a lower dose than in the first treatment regimen, or to discontinue treatment altogether. If the first treatment regimen is determined not to be efficacious, it may be recommended to carry out a second treatment regimen that is different from the first treatment regimen, e.g., it may be recommended to administer a different therapeutic agent than the therapeutic agent administered as part of the first treatment regimen.

For example, in some embodiments, an individual has undergone a treatment regimen for cancer, e.g., radiation treatment, surgical removal of cancerous tissue, chemotherapeutic treatment, or a combination of two or more such treatments. Efficacy of the treatment is determined by detecting cancerous tissue, if any, in the individual, in the days, weeks, months, or years following the treatment for the cancer. Cancerous tissue is detected, as described above, by administering to the individual a composition comprising a functionalized MNP; and detecting binding of the functionalized MNP to tissues in the individual. Depending on the analysis of the efficacy of the treatment regimen, a recommendation is made for: a) discontinuation of treatment; b) an alteration of the treatment regimen, e.g., to increase the dose and/or frequency of treatment; or c) a treatment regimen that is different from the pre-analysis treatment regimen.

For example, in some embodiments, a subject method comprises: a) administering functionalized MNPs at a first time to an individual having cancer, where the individual is being treated with a treatment regimen, where a first image is produced; b) administering to the individual a subject functionalized MNP at a second time to the individual, where the second time is from about 1 day to about 1 year after the first time (e.g., where the second time is from about 1 day to about 2 days, from about 2 days to about 1 week, from about 1 week to about 2 weeks, from about 2 weeks to about 1 month, from about 1 month to about 2 months, from about 2 months to about 4 months, from about 4 months to about 6 months, from about 6 months to about 8 months, or from about 8 months to about 1 year, after the first time); and c) comparing the first and second images produced following the first and the second administrations. Further administrations at further time points are also contemplated. Where the second image, compared to the first image, indicates that the cancer is progressing, medical personnel can recommend a different treatment regimen. Where the second image, compared to the first image, indicates that the cancer is regressing, medical personnel can recommend that the treatment regimen be maintained.

In some embodiments, the progress of the cancer is provided in a report. Thus, in some embodiments, a subject method further includes a step of preparing or generating a report that includes information regarding the disease progression and the treatment efficacy. For example, a subject method can further include a step of generating or outputting a report providing the results of a subject method, which report can be provided in the form of an electronic medium (e.g., an electronic display on a computer monitor), or in the form of a tangible medium (e.g., a report printed on paper or other tangible medium).

Monitoring a Cancer

The present disclosure provides methods of monitoring the progress of a cancer in an individual, the methods generally involving administering to an individual having cancer a composition comprising a functionalized MNP, and detecting binding of the functionalized MNP to a tissue or tissues in the individual. A composition comprising a MNP is administered at various times throughout the course of the disease, to monitor the state of the disease in the individual. For example, the size of a tumor can be monitored. As another example, whether a cancer has metastasized can be monitored.

For example, in some embodiments, a subject method comprises: a) administering functionalized MNPs at a first time to an individual having a cancer, where a first image is produced; b) administering to the individual a subject 2DG-functionalized MNP at a second time to the individual, where the second time is from about 1 day to about 1 year after the first time (e.g., where the second time is from about 1 day to about 2 days, from about 2 days to about 1 week, from about 1 week to about 2 weeks, from about 2 weeks to about 1 month, from about 1 month to about 2 months, from about 2 months to about 4 months, from about 4 months to about 6 months, from about 6 months to about 8 months, or from about 8 months to about 1 year, after the first time); and c) comparing the first and second images produced following the first and the second administrations. Further administrations at further time points are also contemplated. In some embodiments the second image, compared to the first image, will indicate that the cancer is progressing. In some embodiments the second image, compared to the first image, will indicate that the cancer is regressing. In other embodiments, the second image, compared to the first image, will indicate that the cancer is stabilized.

In some embodiments, the disease progress is provided in a report. Thus, in some embodiments, a subject method further includes a step of preparing or generating a report that includes information regarding the disease progression. For example, a subject method can further include a step of generating or outputting a report providing the results of a subject disease monitoring method, which report can be provided in the form of an electronic medium (e.g., an electronic display on a computer monitor), or in the form of a tangible medium (e.g., a report printed on paper or other tangible medium).

Staging or Grading a Cancer

In some embodiments, a subject detection method is useful for staging or grading a cancer. Staging or grading can be correlated to the size of the tumor and/or the metastasis of the tumor. Binding of a functionalized MNP to a tumor in the body is detected, where the detection provides for staging or grading of the tumor. For example, the strength of the signal obtained from detection of tumor-bound functionalize MNP is correlated with stage and/or grade.

In some embodiments, the disease stage is provided in a report. Thus, in some embodiments, a subject method further includes a step of preparing or generating a report that includes information regarding the disease stage. For example, a subject method can further include a step of generating or outputting a report providing the results of a subject cancer staging/grading method, which report can be provided in the form of an electronic medium (e.g., an electronic display on a computer monitor), or in the form of a tangible medium (e.g., a report printed on paper or other tangible medium).

Predictive Methods

A functionalized MNP can also be used as surrogate markers in methods of predicting (determining the likelihood) that an individual will develop a cancer. Thus, the present disclosure provides methods of determining the likelihood that an individual will develop a cancer, the methods generally involving: a) administering to the individual a functionalized MNP; and b) detecting binding of the functionalized MNP to a tissue in the individual; where the results of the detection step can provide for a prediction that the individual has a higher likelihood of developing a cancer than a reference control, or can provide for a prediction that the individual will likely not develop the cancer. In some embodiments, the methods further comprise generating a report that includes the prediction. In some embodiments, the report further includes a treatment recommendation for the individual. In some embodiments, the method further comprises treating the individual.

For example, where the level of binding of a functionalized MNP to a particular tissue is at least about 5%, at least about 10%, at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold, higher than a normal control level (e.g., the level of binding of a functionalized MNP to a tissue that is known not to be cancerous), a prediction can be made that the individual has a likelihood of developing a cancer of or in that tissue, where the likelihood is at least about 25%, at least about 50%, at least about 75%, at least about 100% (or two-fold), at least about 2.5-fold, at least about 5-fold, at least about 10-fold, or greater than 10-fold, higher than the likelihood that a normal, control individual will develop the cancer.

For example, where the level of binding of a functionalized MNP to (or metabolic uptake into) a breast tissue in a female individual (e.g., a female human) is at least about 5%, at least about 10%, at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold, higher than a normal control level (e.g., the level of binding of a functionalized MNP to a breast tissue that is known not to be diseased; the level of metabolic uptake of a functionalized MNP into a breast tissue that is known not to be diseased), a prediction can be made that the individual has a likelihood of developing breast cancer, where the likelihood is at least about 25%, at least about 50%, at least about 75%, at least about 100% (or two-fold), at least about 2.5-fold, at least about 5-fold, at least about 10-fold, or greater than 10-fold, higher than the likelihood that a normal, control individual will develop breast cancer.

For example, where the level of binding of a functionalized MNP to a prostate tissue in a male individual (e.g., a male human) is at least about 5%, at least about 10%, at least about 25%, at least about 50%, at least about 75%, at least about 100% (or two-fold), at least about 2.5-fold, at least about 5-fold, at least about 10-fold, at least about 25-fold, at least about 50-fold, or at least about 100-fold, higher than a normal control level (e.g., the level of binding of a functionalized MNP to a prostate tissue that is known not to be diseased), a prediction can be made that the individual has a likelihood of developing prostate cancer, where the likelihood is at least about 25%, at least about 50%, at least about 75%, at least about 100% (or two-fold), at least about 2.5-fold, at least about 5-fold, at least about 10-fold, or greater than 10-fold, higher than the likelihood that a normal, control individual will develop prostate cancer.

As noted above, in some embodiments, a subject predictive method will further comprise generating a report. For example, a subject method can further include a step of generating or outputting a report providing the results of a subject likelihood assessment, which report can be provided in the form of an electronic medium (e.g., an electronic display on a computer monitor), or in the form of a tangible medium (e.g., a report printed on paper or other tangible medium). The report will include at least the prediction (likelihood assessment), and can include further information such as: a) the results of the detection step; b) personal information about the individual such as age, weight, gender, etc.; c) medical information about the individual, e.g., family history of the disease, prior treatment for a disease, genetic information (e.g., genotyping results relating to the cancer), and the like.

The report can further include a treatment recommendation(s). Where the results indicate a likelihood of cancer development, the recommendation can include a recommendation that a treatment regimen is indicated. Where the results indicate that development of cancer is not likely, the recommendation can include a recommendation for no treatment, or can include a recommendation for further evaluation of the patient. For example, where the individual being tested is a human female, and the results of a subject predictive method (a subject cancer likelihood assessment) indicate that the individual will likely develop breast cancer, the recommendation can include: a) a recommendation that the individual be further evaluated for breast cancer; and/or b) a recommendation that the individual be treated with an anti-cancer agent suitable for treating early stage breast cancer.

Computer-Readable Storage Medium

The present disclosure also contemplates a computer-readable storage medium (e.g. compact disc-read only memory (CD-ROM), memory key, flash memory card, diskette, etc.) having stored thereon a program which, when executed in a computing environment, provides for implementation of a disease likelihood assessment as described above. Where the computer-readable medium contains a complete program for carrying out the methods described herein, the program includes program instructions for collecting, analyzing and generating output, and generally includes computer readable code devices for interacting with a user as described herein, processing that data in conjunction with analytical information, and generating unique printed or electronic media for that user.

The present disclosure further provides a computer-based system that includes a processor-readable medium comprising code representing instructions to generate a prediction of likelihood that an individual will develop a disease, based on data generated by the detection step of a subject predictive method. A subject computer-based system involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which can include test data (e.g., results of an imaging method used to detect functionalized MNP binding to, and/or metabolic uptake into, a tissue in a living individual, as described above); and may also include other data such as patient data. This information received can be stored at least temporarily in a database, and data analyzed to generate a report as described above.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include electronic mail, interactive television, and the like. In an embodiment of particular interest, all or a portion of the input data and/or all or a portion of the output data (e.g., usually at least the final report) are maintained on a web server for access, e.g., confidential access, with typical browsers. The data may be accessed or sent to health professionals as desired. The input and output data, including all or a portion of the final report, can be used to populate a patient's medical record which may exist in a confidential database at the healthcare facility.

Treatment Methods

The present disclosure provides methods of treating a cancer in an individual. In some embodiments, the methods involve administering to an individual in need thereof a pharmaceutical composition comprising: i) a functionalized MNP, wherein the functionalized MNP comprises a first functional moiety that has differential affinity for and/or metabolic uptake into a cancer cell, and a second functional moiety that is a cancer chemotherapeutic agent; and ii) a pharmaceutically acceptable carrier; where the functionalized MNP associates with a cancer cell in the individual, and wherein the cancer chemotherapeutic agent treats the cancer. In other embodiments, a subject method involves: a) administering to the individual a pharmaceutical composition comprising: i) a functionalized MNP, wherein the functionalized MNP comprises a functional moiety that has differential affinity for and/or metabolic uptake into a cancer cell; and ii) a pharmaceutically acceptable carrier; b) detecting the presence of the functionalized MNP in association with the cancerous tissue; and c) carrying out a cancer treatment regimen on the individual.

Suitable cancer treatment regimens include, e.g., hyperthermia therapy on the cancerous tissue, surgery (e.g., surgical removal of cancerous tissue), radiation therapy, laser ablation, hyperthermia therapy, bone marrow transplantation, chemotherapeutic treatment, biological response modifier treatment, and certain combinations of the foregoing. Radiation therapy includes, but is not limited to, x-rays or gamma rays that are delivered from either an externally applied source such as a beam, or by implantation of small radioactive sources. Thus, e.g., in some embodiments, a subject method involves: a) administering to the individual a pharmaceutical composition comprising: i) a functionalized MNP, wherein the functionalized MNP comprises a functional moiety that has differential affinity for and/or metabolic uptake into a cancer cell; and ii) a pharmaceutically acceptable carrier; b) detecting the presence of the functionalized MNP in association with the cancerous tissue, e.g., using an imaging method such as MRI, CT, etc.; and c) applying a hyperthermia treatment regimen to the cancerous tissue. In some embodiments, a subject method involves: a) administering to the individual a pharmaceutical composition comprising: i) a functionalized MNP, wherein the functionalized MNP comprises a functional moiety that has differential affinity for and/or metabolic uptake into a cancer cell; and ii) a pharmaceutically acceptable carrier; b) detecting the presence of the functionalized MNP in association with the cancerous tissue, e.g., using an imaging method such as MRI, CT, etc.; and c) applying a hyperthermia treatment regimen to the cancerous tissue in the individual and administering an effective amount of a cancer chemotherapeutic agent to the individual. In some embodiments, a subject method involves: a) administering to the individual a pharmaceutical composition comprising: i) a functionalized MNP, wherein the functionalized MNP comprises a functional moiety that has differential affinity for and/or metabolic uptake into a cancer cell; and ii) a pharmaceutically acceptable carrier; b) detecting the presence of the functionalized MNP in association with the cancerous tissue, e.g., using an imaging method such as MRI, CT, etc.; and c) administering an effective amount of one or more cancer chemotherapeutic agents to the individual. In some embodiments, a subject method involves: a) administering to the individual a pharmaceutical composition comprising: i) a functionalized MNP, wherein the functionalized MNP comprises a functional moiety that has differential affinity for and/or metabolic uptake into a cancer cell; and ii) a pharmaceutically acceptable carrier; b) detecting the presence of the functionalized MNP in association with the cancerous tissue, e.g., using an imaging method such as MRI, CT, etc.; and c) administering an effective dose of ionizing radiation to the individual. In some embodiments, a subject method involves: a) administering to the individual a pharmaceutical composition comprising: i) a functionalized MNP, wherein the functionalized MNP comprises a functional moiety that has differential affinity for and/or metabolic uptake into a cancer cell; and ii) a pharmaceutically acceptable carrier; b) detecting the presence of the functionalized MNP in association with the cancerous tissue, e.g., using an imaging method such as MRI, CT, etc.; and c) administering an effective dose of ionizing radiation to the individual and administering an effective amount of a cancer chemotherapeutic agent to the individual.

A subject treatment method can involve administering a pharmaceutical composition comprising a functionalized MNP. A pharmaceutical composition comprising a functionalized MNP can comprise one or more pharmaceutically acceptable carriers. As used herein, "pharmaceutically acceptable carrier" includes any material which, when combined with an active ingredient of a composition, allows the ingredient to retain biological activity and without causing disruptive reactions with the subject's immune system or other physiological function. Examples include, but are not limited to, any of the standard pharmaceutical carriers such as a phosphate buffered saline solution, water, emulsions such as oil/water emulsion, and various types of wetting agents. Exemplary diluents for aerosol or parenteral administration are phosphate buffered saline or normal (0.9%) saline. Compositions comprising such carriers are formulated by well known conventional methods (see, for example, Remington's Pharmaceutical Sciences, Chapter 43, 14th Ed., Mack Publishing Col, Easton Pa. 18042, USA). Pharmaceutically acceptable excipients have been amply described in a variety of publications, including, for example, A. Gennaro (2000) "Remington: The Science and Practice of Pharmacy," 20th edition, Lippincott, Williams, & Wilkins; Remington's Pharmaceutical Sciences, 14th Ed. or latest edition, Mack Publishing Col, Easton Pa. 18042, USA; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A functionalized MNP can be formulated into preparations for injection (e.g., intravenous injection, intramuscular injection, subcutaneous injection, ocular injection, etc.), for inhalation, for oral delivery, for delivery through the gastrointestinal tract, for ocular delivery, for topical delivery (e.g., topical delivery to the skin), or for delivery via the genito-urinary tract.

A functionalized MNP can be formulated into preparations for injection by dissolving, suspending or emulsifying in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In some embodiments, a functionalized MNP is formulated as a gel, as a solution, a solid, a semi-solid, or in some other form suitable for intravaginal administration. In a further exemplary embodiment, a functionalized MNP is formulated as a gel, as a solution, a solid, a semi-solid, or in some other form suitable for rectal (e.g., intrarectal) administration.

A functionalized MNP can be formulated for delivery via the genito-urinary tract by formulating the functionalized MNP in a suppository. A functionalized MNP can be made into suppositories by mixing with a variety of bases such as emulsifying bases or water-soluble bases. A functionalized MNP can be administered rectally via a suppository. The suppository can include vehicles such as cocoa butter, carbowaxes and polyethylene glycols, which melt at body temperature, yet are solidified at room temperature. For suppositories, the composition can include traditional binders and carriers such as, polyalkylene glycols, or triglycerides. Such suppositories may be formed from mixtures containing the active ingredient in the range of about 0.5% to about 10% (w/w), e.g. about 1% to about 2%.

A functionalized MNP will in some embodiments be formulated for vaginal delivery. A subject formulation for intravaginal administration can be formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

A functionalized MNP will in some embodiments be formulated for rectal delivery. A subject formulation for intrarectal administration is formulated as an intrarectal bioadhesive tablet, intrarectal bioadhesive microparticle, intrarectal cream, intrarectal lotion, intrarectal foam, intrarectal ointment, intrarectal paste, intrarectal solution, or intrarectal gel.

In some embodiments, a functionalized MNP is formulated for oral delivery. For oral preparations, a functionalized MNP can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A functionalized MNP will in some embodiments be administered to a patient by means of a pharmaceutical delivery system for the inhalation route. A functionalized MNP can be formulated in a form suitable for administration by inhalation. The inhalational route of administration provides the advantage that the inhaled drug can bypass the blood-brain barrier. The pharmaceutical delivery system is one that is suitable for respiratory therapy by delivery of a functionalized MNP to mucosal linings of the bronchi. This invention can utilize a system that depends on the power of a compressed gas to expel the functionalized MNP from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed, the aerosol contains a functionalized MNP, which can be suspended or emulsified in a mixture of a fluid carrier and a propellant. The aerosol can be in the form of a solution, suspension, emulsion, powder, or semi-solid preparation. Aerosols are intended for administration as fine, solid particles or as liquid mists via the respiratory tract of a patient. Various types of propellants known to one of skill in the art can be utilized. Suitable propellants include, but are not limited to, hydrocarbons such as dichlorodifluoromethane, propane, etc.; nitrogen; and the like. In the case of the pressurized aerosol, the dosage unit may be determined by providing a value to deliver a metered amount.

A functionalized MNP can be formulated with a low boiling point propellant. Such formulations are generally administered by conventional meter dose inhalers (MDI's). A functionalized MNP can be formulated in an aqueous or ethanolic solution and delivered by a conventional nebulizer. A functionalized MNP can be formulated into a dry powder formulation. Such a formulation can be administered by simply inhaling the dry powder formulation after creating an aerosol mist of the powder.

A functionalized MNP can be formulated for ocular delivery, e.g., where a functionalized MNP is formulated for delivery to the eye in liquid form (e.g., eye drops), for injection into or around the eye, etc. Ophthalmic pharmaceutical compositions can be adapted for topical administration to the eye in the form of solutions, suspensions, ointments, creams or as a solid insert.

For ocular formulations, a functionalized MNP can be conveniently admixed with a non-toxic pharmaceutical organic carrier, or with a non-toxic pharmaceutical inorganic carrier. Suitable pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethyl-cellulose, polyvinylpyrrolidone, isopropyl myristate and other conventionally employed acceptable carriers. The pharmaceutical preparation can also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitate, dioctyl sodium sulfosuccinate, monothioglycerol, thiosorbitol, ethylenediamine tetracetic acid, and the like.

Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The ocular formulation can also be in the form of a microparticle formulation. The ocular formulation can also be in the form of a solid insert. For example, one may use a solid water soluble polymer as the carrier for the medicament. The polymer used to form the insert can be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyacrylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

A formulation comprising a functionalized MNP can further include one or more non-toxic auxiliary substances such as antibacterial components which are non-injurious in use, for example, thimerosal, benzalkonium chloride, methyl and propyl paraben, benzyldodecinium bromide, benzyl alcohol, chlorhexidine, or phenylethanol; buffering ingredients such as sodium borate, sodium acetate, sodium citrate, or gluconate buffers; and other conventional ingredients such as sodium chloride, sorbitan monolaurate, triethanolamine, polyoxyethylene sorbitan monopalmitate, ethylenediaminetetraacetic acid, and the like.

A functionalized MNP can be formulated for topical administration to the skin. For example, a functionalized MNP can be formulated with one or more dermatologically acceptable excipients. The term "dermatologically acceptable," as used herein, means that the compositions or components thereof so described are suitable for use in contact with human skin without undue toxicity, incompatibility, instability, allergic response, and the like.

In some embodiments, a functionalized MNP is formulated with a dermatologically active acid. Suitable dermatologically active acids include a hydroxy acid, ascorbic acid, glycolic acid, magnesium ascorbyl phosphate, sodium ascorbyl phosphate, sodium ascorbate, ascorbyl glucosides, salicylic acid, lipoic acid, dihydrolipoic acid, and combinations thereof. In some embodiments, the dermatologically active acid is alpha-hydroxy acid. Alpha-hydroxy acids include, malic acid, tartaric acid, lactic acid, pyruvic acid, citric acid, and combination of any of the foregoing. In some embodiments, a functionalized MNP is formulated with a dermatologically active acid and one or more of: ammonium hydroxide, alkali hydroxide, alkanolamone, amino acid, sodium hydroxide, potassium hydroxide, diethanolamine, triethanolamine, 2-dimethylaminoethanol (dimethyl MEA), aminobutanol, arginine, and lysine.

Suitable excipients to topical formulations (e.g., for topical application to the skin) include emollients; humectants; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); sugar and starch derivatives (e.g., alkoxylated glucose); hyaluronic acid; lactamide monoethanolamine; acetamide monoethanolamine; and the like.

In some embodiments, the functionalized MNP further comprises an apolipoprotein (e.g., apoA, apoB, or apoE) attached to the functionalized MNP. The apolipoprotein provides for binding to endothelial cells of the BBB, and thus provides for transit of the functionalized MNP across the BBB.

In some embodiments, the functionalized MNP is further processed by attaching human serum albumin and/or apolipoprotein to the functionalized MNP. Human serum albumin (HSA) is attached, covalently or non-covalently (e.g., via ionic interactions) to the functionalized MNP via an acetyl group, via an amino group, via a poly(ethylene glycol) (PEG) linker, or via a thiol bond. Apolipoprotein, or a functional fragment thereof, is attached to the HSA, either covalently or non-covalently. See, e.g. Muller and Keck ((2004) *J. Nanosci. Nanotechnol.* 4:471); and Kreuter et al. ((2002) *J. Drug Target.* 10:317). Amino acid sequences of apolipoproteins are known in the art; for example, amino acid sequences of apoE polypeptides are found at e.g., GenBank Accession Nos. AAD02505; and AAB59397.

In other embodiments, the functionalized MNP further comprises apolipoprotein attached to the functionalized MNP via polysorbate-80. In some embodiments, the functionalized MNP is further processed by attaching polysorbate-80 covalently or non-covalently to the functionalized MNP. In some embodiments, the polysorbate-80 is attached via an acetyl group, via an amino group, via a PEG linker, or via a thiol bond directly to the coating layer. Apolipoprotein is attached to the polysorbate-80, either covalently or non-covalently.

In some embodiments, a functionalized MNP is administered in an amount (e.g., number of functionalized MNPs) that is effective for detection of a cancer cell. In other embodiments, a functionalized MNP is administered in an amount (e.g., a number of functionalized MNPs) that is effective to treat the cancer, e.g., where the functionalized MNP comprises a first functional moiety that provides for differential affinity for and/or differential metabolic uptake into a cancer cell and a second functional moiety that is a cancer chemotherapeutic agent. In some embodiments, an effective amount of a functionalized MNP is an amount that is sufficient to reduce the size of a tumor by at least about 10%, at least about 20%, at least about 25%, at least about 30%, at least about 40%, at least about 50%, at least about 60%, at least about 70%, at least about 80%, at least about 90%, or more, compared to the size of the tumor in an individual not treated with the functionalized MNP, or compared to the size of the tumor in an individual before treatment with the functionalized MNP.

A suitable unit dose of functionalized MNP ranges from about $10^2$ functionalized MNP to about $10^{18}$ functionalized MNP, e.g., from about $10^2$ to about $10^3$ functionalized MNP, from about $10^3$ to about $10^4$ functionalized MNP, from about $10^4$ to about $10^5$ functionalized MNP, from about $10^5$ to about $10^6$ functionalized MNP, from about $10^6$ to about $10^7$ functionalized MNP, from about $10^7$ to about $10^8$ functionalized MNP, from about $10^8$ to about $10^9$ functionalized MNP, from about $10^9$ functionalized MNP to about $10^{10}$ functionalized MNP, from about $10^{10}$ functionalized MNP to about $10^{12}$ functionalized MNP, from about $10^{12}$ functionalized MNP to about $10^{14}$ functionalized MNP, from about $10^{14}$ functionalized MNP to about $10^{16}$ functionalized MNP, or from about $10^{16}$ functionalized MNP to about $10^{18}$ functionalized MNP.

In some embodiments, a unit dose of a functionalized MNP is expressed on the basis of the weight of the patient. For example, in some embodiments, a unit dose of a functionalized MNP is from about 0.5 mg/kg to about 50 mg/kg, e.g., from about 0.5 mg/kg to about 1 mg/kg, from about 1 mg/kg to about 2.5 mg/kg, from about 2.5 mg/kg to about 5 mg/kg, from about 5 mg/kg to about 10 mg/kg, from about 10 mg/kg to about 15 mg/kg, from about 15 mg/kg to about 20 mg/kg, from about 20 mg/kg to about 25 mg/kg, from about 25 mg/kg to about 30 mg/kg, from about 30 mg/kg to about 35 mg/kg, from about 35 mg/kg to about 40 mg/kg, from about 40 mg/kg to about 45 mg/kg, or from about 45 mg/kg to about 50 mg/kg.

In some embodiments, multiple doses of a functionalized MNP will be administered. For example, a unit dose of a functionalized MNP will be administered is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

In some embodiments, a functionalized MNP is administered at any suitable frequency, and over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

A composition comprising a functionalized MNP can be administered to an individual via a parenteral route of administration, e.g., intravenous, intramuscular, subcutaneous, intratumoral, intracranial, peritumoral, inhalational, ocular, topical (e.g., to the skin), via the genito-urinary tract, etc. A composition comprising a functionalized MNP can be administered to an individual via an enteral route of administration, e.g., via an oral route of administration, via a gastrointestinal route of administration, or via rectal administration.

In some embodiments, a pharmaceutical composition comprising a functionalized MNP is administered to an individual in need thereof, where the functionalized MNP comprises a therapeutic agent. In some embodiments, a pharmaceutical composition comprising a functionalized MNP is administered to an individual in need thereof, where the functionalized MNP comprises a therapeutic agent, where the route of administration is parenteral, e.g., intravenous, intramuscular, subcutaneous, intratumoral, intracranial, peritumoral, ocular, topical (e.g., to the skin), via inhalation, via the genito-urinary tract, etc. In some embodiments, a pharmaceutical composition comprising a functionalized MNP is administered to an individual in need thereof, where the functionalized MNP comprises a therapeutic agent, where the route of administration is enteral, e.g., oral, rectal, via the gastrointestinal tract, etc.

Subjects Suitable for Diagnosis or Treatment

An individual who is to be subjected to a subject diagnostic method is in some embodiments an individual who has not been diagnosed as having a cancer. In some embodiments, an individual who is to be subjected to a subject diagnostic method is an individual who has been diagnosed as having a cancer, by a method other than a subject method, e.g., a subject method is meant to provide confirmation of a previous diagnosis.

In some embodiments, an individual who is to be subjected to a subject diagnostic method is an individual in whom diagnosis using a radioactive substance is contraindicated, e.g., a pediatric patient, a pregnant woman, and the like.

In some embodiments, an individual who is treated with a subject treatment method is an individual who has previously undergone a cancer treatment other than a subject treatment, and who has not responded to the previous treatment (a "non-responder"), or who initially responded to the previous treatment but relapsed, e.g., experienced a recurrence of the cancer (a "relapse").

Functionalized MNPs

The present disclosure provides functionalized MNPs that exhibit differential binding to a tumor, and compositions, including pharmaceutical compositions, comprising the functionalized MNPs. In some embodiments, a subject functionalized MNP comprises a functional group that provides for selective binding (differential affinity) to an adrenal gland tissue (e.g., an adrenal dysplasia or an adrenal tumor). In other embodiments, a subject functionalized MNP comprises a functional group that provides for selective binding (differential affinity) for a pituitary tissue (e.g., a pituitary tumor).

The present disclosure provides functionalized magnetic nanoparticles (MNPs) that comprises a least one functional moiety, e.g., comprising at least one functional moiety that provides for differential affinity for a pituitary tissue (e.g., a pituitary tumor), or comprising at least one functional moiety that provides for differential affinity for an adrenal gland tissue (e.g., an adrenal dysplasia or an adrenal tumor). In some embodiments, a subject functionalized MNP comprises only an ACTH polypeptide as a functional moiety. In some embodiments, a subject functionalized MNP comprises only a CRF polypeptide as a functional moiety. In other embodiments, a subject functionalized MNP comprises, in addition to an ACTH polypeptide or a CRF polypeptide, at least a second functional moiety.

A subject functionalized MNP comprises an MNP and one or more functional groups, where the one or more functional groups includes at least at least one functional moiety that provides for differential affinity for a pituitary tissue (e.g., a pituitary tumor), or at least one functional moiety that provides for differential affinity for an adrenal gland tissue (e.g., an adrenal dysplasia or an adrenal tumor). The MNP comprises a magnetic core particle and a biocompatible substrate. The one or more functional groups is linked to the biocompatible substrate, either directly or via a linker. The combination of the biocompatible substrate and the one or more functional groups is referred to herein as the "coating."

Suitable biocompatible substrates include, but are not limited to, polysaccharides and oligosaccharides, and derivatives thereof, including, e.g., dextran, an iron-dextran complex, carboxymethyl dextran, starch, dialdehyde starch, chitin, alginate, cellulose, and carboxymethylcellulose; a polymer, including e.g., a polyethylene glycol, a polyethylene oxide, a poloxamer, a poloxamine, polystyrene, polyethylene, polyvinyl chloride, polyvinylpyrrolidone, polyethyleneimine, a polymethylacrylate, a polyvinyl alcohol, and an acrylic polymer; a phospholipid; a compound such as silica, aluminum silica, a silicone, etc.; and proteins and derivatives thereof, including, e.g., albumin, synthetic proteins, etc.

A subject functionalized MNP exhibits differential affinity for a mammalian tissue. In some embodiments, the mammalian tissue is human tissue. In other embodiments, the mammalian tissue is a non-human primate tissue. In other embodiments, the mammalian tissue is a rodent (e.g., mouse, rat, etc.) tissue. In other embodiments, the mammalian tissue is a tissue of a canine, a feline, an ungulate (e.g., an equine, a bovine, an ovine, and the like), or other non-human mammal. A subject functionalized MNP allows imaging of a tissue in a living individual, e.g., a living mammal (e.g., a living rodent, a living human, a living non-human primate, a living ungulate, a living canine, a living feline, etc.). A subject functionalized MNP allows imaging of a tissue in a living individual without the need for radioactivity. Thus, in some embodiments, a subject functionalized MNP does not comprises any radioactive moieties. A subject functionalized MNP can include a radioactive moiety, but in many embodiments will not include any radioactive moiety.

In some embodiments, a subject functionalized MNP exhibits differential affinity for a particular mammalian tissue. In some embodiments, a subject functionalized MNP exhibits differential affinity for a diseased mammalian tissue, e.g., a subject functionalized MNP exhibits an affinity for a diseased tissue that is at least about 25%, at least about 50%, at least about 100% (or 2-fold), at least about 2.5-fold, at least about 5-fold, at least about 10-fold, at least about 15-fold, at least about 20-fold, at least about 50-fold, or at least about 100-fold, or more, higher than the affinity of the functionalized MNP for a non-diseased tissue, e.g., for a non-diseased tissue of the same tissue type. For example, in some embodiments, a subject ACTH-functionalized MNP exhibits differential affinity for an adrenal tissue, e.g., a subject ACTH-functionalized MNP exhibits an affinity for an adrenal tissue that is at least about 25%, at least about 50%, at least about 100% (or 2-fold), at least about 2.5-fold, at least about 5-fold, at least about 10-fold, at least about 15-fold, at least about 20-fold, at least about 50-fold, or at least about 100-fold, or more, higher than the affinity of the ACTH-functionalized MNP for a non-adrenal tissue. As another example, in some embodiments, a subject CRF-functionalized MNP exhibits differential affinity for a pituitary tissue (e.g., a pituitary tumor), e.g., a subject CRF-functionalized MNP exhibits an affinity for a pituitary that is at least about 25%, at least about 50%, at least about 100% (or 2-fold), at least about 2.5-fold, at least about 5-fold, at least about 10-fold, at least about 15-fold, at least about 20-fold, at least about 50-fold, or at least about 100-fold, or more, higher than the affinity of the CRF-functionalized MNP for a non-pituitary tissue.

Tissues that can be detected using a subject ACTH-functionalized MNP include, but are not limited to, adrenal gland tissue; an adrenal dysplasia; and an adrenal tumor. An adrenal tissue, adrenal dysplasia, or adrenal tumor can be detected in utero; in a neonate; in a pediatric subject; or in an adult. An adrenal tissue can also be detected after regeneration or transplant.

Tissues that can be detected using a subject CRF-functionalized MNP include, but are not limited to, a pituitary tissue; and a pituitary tumor.

In some embodiments, a subject functionalized MNP comprises an ACTH polypeptide as a functional moiety. A suitable ACTH polypeptide can comprise an amino acid sequence having at least about 75%, at least about 80%, at least about 85%, at least about 90%, at least about 95%, at least about 98%, at least about 99%, or 100%, amino acid sequence identity to a contiguous stretch of from 30 amino acids to 39 amino acids of the following sequence: sysmehfrwg kpvgkkrrpv kvypngaede saeafplef (SEQ ID NO:4). A suitable ACTH polypeptide binds an ACTH receptor on cell in a target tissue. A suitable ACTH polypeptide is a variant ACTH polypeptide that comprises one or more amino acid substitutions compared to the amino acid sequence set forth in SEQ ID NO:4, where the variant binds an ACTH receptor. For example, in some embodiments, a suitable ACTH polypeptide will have a Val instead of Leu at position 37 of SEQ ID NO:4. As another example, in some embodiments, a suitable ACTH polypeptide will have an Asp instead of a Glu at position 38 of SEQ ID NO:4. As another example, in some embodiments, a suitable ACTH polypeptide will have a Gln instead of a Glu at position 33 of SEQ ID NO:4. A suitable ACTH polypeptide can include heterologous amino acids, e.g., amino acids not normally associated with ACTH. In some embodiments, the ACTH polypeptide has a length of from about 30 amino acids to about 40 amino acids, from about 40 amino acids to about 50 amino acids, or from about 50 amino acids to about 100 amino acids. In some embodiments, a subject functionalized MNP that comprises ACTH as a functional group exhibits differential binding to adrenal dysplasia or to an adrenal tumor.

In some embodiments, a subject functionalized MNP comprises a CRF polypeptide as a functional moiety. In some embodiments, the functional moiety is a corticotropin releasing factor (CRF) polypeptide. A suitable CRF polypeptide can comprise an amino acid sequence having at least about 75%, at least about 80%, at least about 85%, at least about 90%, at least about 95%, at least about 98%, at least about 99%, or 100%, amino acid sequence identity to a contiguous stretch of from 30 amino acids to 41 amino acids of the following sequence: seeppisldl tfhllrevle maraeqlaqq ahsnrklmei (SEQ ID NO:5). A suitable CRF polypeptide binds a CRF receptor on cell in a target tissue. A suitable CRF polypeptide is a variant CRF polypeptide that comprises one or more amino acid substitutions compared to the amino acid sequence set forth in SEQ ID NO:5, where the variant binds a CRF receptor. For example, in some embodiments, a suitable CRF polypeptide will have an Ala instead of Ser at position 1 of the amino acid sequence set forth in SEQ ID NO:5. As another example, in some embodiments, a suitable CRF polypeptide will have an Ile instead of Leu at position 27 of the amino acid sequence set forth in SEQ ID NO:5. As another example, in some embodiments, a suitable CRF polypeptide will have an Asp instead of Glu at position 39 of the amino acid sequence set forth in SEQ ID NO:5. A suitable CRF polypeptide can include heterologous amino acids, e.g., amino acids not normally associated with CRF. In some embodiments, the CRF polypeptide has a length of from about 30 amino acids to about 40 amino acids, from about 40 amino acids to about 50 amino acids, or from about 50 amino acids to about 100 amino acids. In some embodiments, a functionalized MNP that comprises CRF as a functional group exhibits differential binding to a pituitary tumor.

In some embodiments, an ACTH polypeptide or a CRF polypeptide is attached to the MNP, directly or via a linker. In some embodiments, an ACTH polypeptide or a CRF polypeptide is attached to a biocompatible substrate, directly or via a linker. Methods for attaching an ACTH polypeptide or a CRF polypeptide to an MNP or to a biocompatible substrate attached to or surrounding a magnetic nanoparticle are known in the art. In some embodiments, an ACTH polypeptide or a CRF polypeptide is attached via the carboxyl-terminal COOH group of the ACTH polypeptide or the CRF polypeptide. In some embodiments, an ACTH polypeptide or a CRF polypeptide is attached via the amino-terminal $NH_3$ group of the ACTH polypeptide or the CRF polypeptide. In other embodiments, an ACTH polypeptide or a CRF polypeptide via an amino acid side chain of an internal amino acid, a carboxyl-terminal amino acid, or an amino-terminal amino acid. Amino acid side chains that are suitable for linkage include, but are not limited to, lysine (e.g., epsilon amino group of lysine), cysteine (e.g., sulfhydryl group of cysteine), etc.

Exemplary methods are depicted in the Examples. For example, in some embodiments, a magnetic nanoparticle is dextran coated, where the dextran is a biocompatible substrate for attachment of an ACTH polypeptide or a CRF polypeptide. Various known chemistries can be used to attach a polypeptide (an ACTH polypeptide or a CRF polypeptide) to a biocompatible substrate such as dextran, e.g., via maleimide, via epoxy, etc.

In some embodiments, conjugation of an ACTH polypeptide or a CRF polypeptide to an MNP increases the potency of the ACTH polypeptide or the CRF polypeptide. In some embodiments, conjugation of an ACTH polypeptide or a CRF polypeptide to an MNP increases the efficacy of an ACTH polypeptide or a CRF polypeptide. In some embodiments, conjugation of an ACTH polypeptide or a CRF polypeptide to an MNP decreases the potency and increases the efficacy of the ACTH polypeptide or the CRF polypeptide. For example, in some embodiments, conjugation of a CRF polypeptide to an MNP increases the efficacy of the CRF polypeptide, e.g., the efficacy in stimulating production of cyclic AMP (cAMP) in a pituitary cell, by at least about 5%, at least about 10%, at least about 25%, at least about 50%, at least about 100% (or 2-fold), at least about 2.5-fold, at least about 5-fold, at least about 10-fold, or more than 10-fold, compared with the efficacy of unconjugated CRF.

Magnetic Nanoparticles

Subject nanoparticles generally have a mean size in a range of from about 1 nm to about 1500 nm, e.g., from about 1 nm to about 10 nm, from about 10 nm to about 50 nm, from about 50 nm to about 100 nm, from about 100 nm to about 250 nm, from about 250 nm to about 500 nm, from about 500 nm to about 750 nm, or from about 750 nm to about 1500 nm. Average diameters will in some embodiments range from about 10 nm to about 1500 nm, e.g., from about 10 nm to about 20 nm, from about 20 nm to about 40 nm, from about 40 nm to about 60 nm, from about 60 nm to about 80 nm, from about 80 nm to about 100 nm, from about 100 nm to about 200 nm, from about 200 nm to about 400 nm, from about 400 nm to about 600 nm, from about 600 nm to about 800 nm, from about 800 nm to about 1000 nm, or from about 1000 nm to about 1500 nm. This size refers to the magnetic core particle plus the coating (e.g., biocompatible substrate plus one or more functional moieties).

The magnetic core particle can have a diameter of from about 1 nm to about 1000 nm, e.g., from about 10 nm to about 20 nm, from about 20 nm to about 40 nm, from about 40 nm to about 60 nm, from about 60 nm to about 80 nm, from about 80 nm to about 100 nm, from about 100 nm to about 200 nm, from about 200 nm to about 400 nm, from about 400 nm to about 600 nm, from about 600 nm to about 800 nm, or from about 800 nm to about 1000 nm.

The coating can have a thickness (e.g., the average distance from the outside surface of the core magnetic particle to the outside surface of the coating) of from about 1 nm to about 500 nm, e.g., from about 1 nm to about 5 nm, from about 5 nm to about 10 nm, from about 10 nm to about 15 nm, from about 15 nm to about 20 nm, from about 20 nm to about 25 nm, from about 25 nm to about 30 nm, from about 30 nm to about 40 nm, from about 40 nm to about 50 nm, from about 50 nm to about 60 nm, from about 60 nm to about 70 nm, from about 70 nm to about 80 nm, from about 80 nm to about 90 nm, from about 90 nm to about 100 nm, from about 100 nm to about 125 nm, from about 125 nm to about 150 nm, from about 150 nm to about 175 nm, from about 175 nm to about 200 nm, from about 200 nm to about 225 nm, from about 225 nm to about 250 nm, from about 250 nm to about 275 nm, from about 275 nm to about 300 nm.

The ratio of the thickness of the coating to the diameter of the magnetic core particle is from about 1:1 to about 1:1000, e.g., from about 1:1 to about 1:1.5, from about 1:1.5 to about 1:2, from about 1:2 to about 1:2.5, from about 1:2.5 to about 1:5, from about 1:5 to about 1:10, from about 1:10 to about 1:25, from about 1:25 to about 1:50, from about 1:50 to about 1:100, from about 1:100 to about 1:250, from about 1:250 to about 1:500, from about 1:500 to about 1:750, or from about 1:750 to about 1:1000.

The diameter of the magnetic core of a subject functionalized MNP can be from about 1% to about 99% of the diameter of the entire functionalized MNP, e.g., the diameter of the magnetic core of a subject functionalized MNP can be from about 1% to about 5%, from about 5% to about 10%, from about 10% to about 25%, from about 25% to about 50%, from about 50% to about 75%, or from about 75% to about 99% of the diameter of the entire functionalized MNP.

The weight of the magnetic core of a subject functionalized MNP can be from about 1% to about 99% of the weight of the entire functionalized MNP, e.g., the weight of the magnetic core of a subject functionalized MNP can be from about 1% to about 5%, from about 5% to about 10%, from about 10% to about 25%, from about 25% to about 50%, from about 50% to about 75%, or from about 75% to about 99% of the weight of the entire functionalized MNP.

One or more properties of a subject functionalized MNP can vary, depending on the ratio of the diameter of the magnetic core to the diameter of the entire functionalized MNP. Such properties include, e.g., blood circulation time, resonance heating properties, transport across various tissues, transport across an endothelial cell layer, transport across the blood-brain barrier, particle clearance time, particle metabolism time, exposure of the core particle, MRI enhancement properties such as effect on T1, T2, T2*, effect on relaxation times of the particle in an externally applied magnetic field, and the like.

Nanoparticles can be simple aggregations of molecules or they can be structured into two or more layers of different substances. For example, simple nanoparticles consisting of magnetite or maghemite are suitable for use. See, e.g., Scientific and Clinical Applications of Magnetic Microspheres, U. Hafeli, W. Schutt, J. Teller, and M. Zborowski (eds.) Plenum Press, New York, 1997; and Tiefenauer et al., Bioconjugate Chem. 4:347, 1993. More complex nanoparticles can consist of a core made of one substance and one or more shells made of another substance(s). The term "magnetic nanoparticle" includes paramagnetic nanoparticles, diamagnetic nanoparticles, and ferromagnetic nanoparticles.

Exemplary core materials that are suitable for inclusion in a subject functionalized MNP include ferrites of general composition $MeO_xFe_2O_3$ wherein Me is a bivalent metal such as Co, Au, Mn or Fe. Other suitable materials are $\gamma$-$Fe_2O_3$, the pure metals Co, Fe, Ni, and metal compounds such as carbides and nitrides. The core material is generally an MRI visible agent. The core material is typically coated. Suitable coatings include, but are not limited to, dextran, albumin, starch, silicon, and the like.

Many different type of small particles (nanoparticles or micron-sized particles) are commercially available from several different manufacturers including: Bangs Laboratories (Fishers, Ind.); Promega (Madison, Wis.); Dynal Inc. (Lake Success, N.Y.); Advanced Magnetics Inc. (Surrey, U.K.); CPG Inc. (Lincoln Park, N.J.); Cortex Biochem (San Leandro, Calif.); European Institute of Science (Lund, Sweden); Ferrofluidics Corp. (Nashua, N.H.); FeRx Inc.; (San Diego, Calif.); Immunicon Corp.; (Huntingdon Valley, Pa.); Magnetically Delivered Therapeutics Inc. (San Diego, Calif.); Miltenyi Biotec GmbH (USA); Microcaps GmbH (Rostock, Germany); PolyMicrospheres Inc. (Indianapolis, Ind.); Scigen Ltd. (Kent, U.K.); Seradyn Inc.; (Indianapolis, Ind.); and Spherotech Inc. (Libertyville, Ill.). Such particles can be made using conventional techniques, such as grinding and milling, emulsion polymerization, block copolymerization, and microemulsion.

Methods of making silica nanoparticles have also been reported. The processes involve crystallite core aggregation (Philipse et al., Langmuir, 10:92, 1994); fortification of superparamagnetic polymer nanoparticles with intercalated silica (Gruttner, C and J Teller, Journal of Magnetism and Magnetic Materials, 194:8, 1999); and microwave-mediated self-assembly (Correa-Duarte et al., Langmuir, 14:6430, 1998).

The core of a subject functionalized MNP is magnetic and can include a metal selected from the group consisting of magnetite, maghemite, and greigite. Magnetic nanoparticles can be made using magnetic materials such as magnetite, maghemite, and greigite as part of the core. By varying the overall size and shape of such magnetic cores, they can be made superparamagnetic or stable single-domain (particles that retain a stable magnetic moment after being removed from a magnetic field). Core size relates to whether a magnetic nanoparticle is superparamagnetic or single-domain. Thus, relatively equidimensional superparamagnetic particles generally have a core sized less than 50 to 80 nm. At particle sizes above this upper range, the magnetization of the particle is split into domains of differing magnetization vectors in order to minimize internal magnetic energies.

In some embodiments, the core includes a pigment which can be an inorganic salt such as potassium permanganate, potassium dichromate, nickel sulfate, cobaltchloride, iron (III) chloride, or copper nitrate. Similarly, the core can include a dye such as Ru/Bpy, Eu/Bpy, or the like; or a metal such as Ag and Cd.

In some embodiments, the core includes a component selected from graphite, a graphite derivative, a carbon compound, a metal carbide, silicon carbide, and the like. For example, in some embodiments, the core includes maghemite, and a component selected from graphite, a graphite derivative, a carbon compound, a metal carbide, silicon carbide, and the like.

In some embodiments, a subject functionalized nanoparticle comprises a core and a silica shell enveloping the core. A functional group is conjugated to the silica shell, e.g., as described in U.S. Pat. No. 6,548,264. Numerous known methods for attaching functional groups to silica can be adapted for use in the present disclosure. See, e.g., Ralph K. Iler, The Chemistry of Silica: Solubility, Polymerization, Colloid and Surface Properties, and Biochemistry, Wiley-Interscience, NY, 1979; VanDerVoort, P. and Vansant, E. F., Journal of Liquid Chromatography and Related Technologies, 19:2723-2752, 1996; and Immobilized Enzymes. Antigens, Antibodies, and Peptides: Preparation and Characterization, Howard H. Weetall (ed.), M. Dekker, NY, 1975. An exemplary process for adding functional groups to silica-coated nanoparticles involves treating the nanoparticles with a silanizing agent that reacts with and couples a chemical group to the silica surface of the nanoparticles. The chemical group can itself be the functional group, or it can serve as a substrate to which functional groups can be coupled.

For example, in an exemplary method, silica-coated nanoparticles are prepared as described above and the particle surfaces are silanized using trimethylsilylpropyl-diethylenetriamine (DETA), a silanization agent that attaches primary amine groups to silica surfaces. Antibodies or other proteins can then be covalently coupled to the silanized surface using the cyanogen bromide (CNBr) method. As one example, CNBr-mediated coupling can be achieved by suspending silica-coated nanoparticles previously silanized with DETA in a 2 M sodium carbonate buffer and ultrasonicating the mixture to create a particle suspension. A solution of CNBr (e.g., 2 g CNBr/1 ml acetonitirile) is then added to the particle suspension to activate the nanoparticles. After washing the nanoparticles with a neutral buffer (e.g., PBS, pH 8), an antibody solution is added to the activated nanoparticle suspension causing the antibodies to become bound to the nanoparticles. A glycine solution can also be added to the antibody-coated nanoparticles to block any remaining unreacted sites.

In some embodiments, the magnetic nanoparticle is dextran coated. Magnetic nanoparticles are made using any known process. For example, magnetic iron-dextran particles can be prepared by mixing 10 ml of 50% (w/w) aqueous Dextran T-40 (Pharmacia) with an equal volume of an aqueous solution containing 1.51 g $FeCl_3$-$6H_2O$ and 0.64 g $FeCl_2$-$4H_2O$. While stirring, the mixture is titrated to pH 10-11 by the drop-wise addition of 7.5% (v/v) $NH_4OH$ heated to 60-65° C. in a water bath for 15 minutes. Aggregates are then removed by 3 cycles of centrifugation in a low-speed clinical centrifuge at 600×g for 5 minutes. The ferromagnetic iron-dextran particles are separated from unbound dextran by gel filtration chromatography on Sephacryl-300. Five ml of the reaction mixture is then applied to a 2.5×33 cm column and eluted with 0.1 M sodium acetate and 0.15 M NaCl at pH 6.5. The purified ferromagnetic iron-dextran particles collected in the void volume will have a concentration of 7-10 mg/ml as determined by dry weight analysis. Molday and Mackenzie (1982) Journal of Immunological Methods 52:353-367. Also see (Xianqiao (2003) China Particuology Vol. 1, No. 2, 76-79).

In some embodiments, a subject functionalized magnetic nanoparticle is of the formula: M-(L)-Z, the linkage sites between L and Z having covalently bound functional groups, wherein M represents the magnetic core particle, L represents an optional linker group, and Z represents a functional group. In other embodiments, a subject functionalized magnetic nanoparticle is of the formula: M-S-(L)-Z, the linkage sites between S and L and L and Z having covalently bound functional groups, wherein M represents the magnetic core particle, wherein S represents a biocompatible substrate fixed to M, wherein M represents the magnetic core particle, L represents an optional linker group, and Z represents a functional group. In some embodiments, a subject functionalized magnetic nanoparticle is of the formula: M-(L)-Z, where M represents the magnetic core particle, where L represents an optional linker group, and where Z represents a functional group. In other embodiments, a subject functionalized magnetic nanoparticle is of the formula: M-S-(L)-Z, where M represents the magnetic core particle, where S represents a biocompatible substrate surrounding M or attached to M, where L represents an optional linker group, and where Z represents a functional group. Functional groups include moieties that provide for binding to a specific tissue type or cell type; moieties that provide for crossing the blood-brain barrier (BBB); therapeutic agents; and the like.

In some embodiments, a subject functionalized magnetic nanoparticle comprises two or more different functional groups attached to the same core particle or to the same biocompatible substrate surrounding or attached to the core particle. For example, in some embodiments, a subject functionalized magnetic nanoparticle is of the formula M-(L)-$Z_1Z_2$, or M-S-(L)-$Z_1Z_2$, where $Z_1$ and are different functional groups, where M is a magnetic core particle, and where L, if present, is a linker. In some embodiments, for example, $Z_1$ is a 2DG moiety and $Z_2$ is a therapeutic agent. In other embodiments, for example, $Z_1$ is an ACTH or a CRF moiety, and $Z_2$ is a therapeutic agent. In other embodiments, for example, $Z_1$ is an ACTH or a CRF moiety; and $Z_2$ is a moiety that provides for crossing the blood-brain barrier (BBB). In some embodiments, a subject functionalized magnetic nanoparticle is of the formula M-S-(L)-$Z_1Z_2$, where M is a magnetic core particle, where the moieties $Z_1$ and $Z_2$ are each linked to the substrate (S), either directly or via a linker (L) (e.g., L, if present, is a linker). In some embodiments, a subject functionalized magnetic nanoparticle comprises at least a third functional moiety $Z_3$. Thus, e.g., in some embodiments, a subject functionalized magnetic nanoparticle is of the formula M-S-(L)-$Z_1Z_2Z_3$, where the moieties $Z_1$, $Z_2$, and $Z_3$ are each linked to the substrate, either directly or via a linker. In some embodiments, $Z_1$ is an ACTH or a CRF moiety; $Z_2$ is a first therapeutic agent; and $Z_3$ is a second therapeutic agent. In other embodiments, $Z_1$ is an ACTH or a CRF moiety; $Z_2$ is a therapeutic agent; and $Z_3$ is a moiety that provides for crossing the BBB.

In some embodiments, the magnetic core particles consist of magnetite, maghemite, ferrites of general formula $MeO_xFe_2O_3$ wherein Me is a bivalent metal such as cobalt, gold, manganese, iron, or of cobalt, iron, nickel, iron carbide, or iron nitride, as described above. If present, the substrate S is a biocompatible substrate comprising one or more compounds such as polysaccharides or oligosaccharides or derivatives thereof, such as dextran, carboxymethyldextran, starch, dialdehyde starch, chitin, alginate, cellulose, carboxymethylcellulose; proteins or derivatives thereof, such as albumins, peptides, synthetic polypeptides, and polypeptides modified with a non-amino acid group such as a sugar, a lipid, a polysaccharide, a phosphate group, etc.; synthetic polymers, such as polyethyleneglycols, polyvinylpyrrolidone, polyethyleneimine, polymethacrylates, bifunctional carboxylic acids and derivatives thereof, such as mercaptosuccinic acid or hydroxycarboxylic acids.

The linker group L can be formed by reaction of a compound such as poly- and dicarboxylic acids, polyhydroxycarboxylic acids, diamines, amino acids, peptides, proteins, lipids, lipoproteins, glycoproteins, lectins, oligosaccharides, polysaccharides, oligonucleotides and alkylated derivatives thereof, and nucleic acids (DNA, RNA, PNA) and alkylated derivatives thereof, present either in single-stranded or double-stranded form, which compound includes at least two identical or different functional groups.

In some embodiments, a subject functionalized magnetic nanoparticle is capable of passing the blood-brain barrier. For example, a subject functionalized magnetic nanoparticle may comprise, attached to the nanoparticle, or in a formulation with the nanoparticle, or coating the nanoparticle, one or more polymers. Suitable polymers that facilitate crossing of the blood brain barrier include, but are not limited to, surfactants such as polysorbate (e.g., Tween® 20, 40, 60 and 80); poloxamers such as Pluronic® F 68; and the like. In some embodiments, a subject functionalized magnetic nanoparticle is coated with a polysorbate such as, e.g., Tween® 80 (which is Polyoxyethylene-80-sorbitan monooleate), Tween® 40 (which is Polyoxyethylene sorbitan monopalmitate); Tween® 60 (which is Polyoxyethylene sorbitan monostearate); Tween® 20 (which is Polyoxyethylene-20-sorbitan monolaurate); polyoxyethylene 20 sorbitan monopalmitate; polyoxyethylene 20 sorbitan monostearate; polyoxyethylene 20 sorbitan monooleate; etc. Also suitable for use are water soluble polymers, including, e.g.: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly (vinyl pyrrolidinone) ("PVP"); poly(amino acids); dextran, and proteins such as albumin. Block co-polymers are suitable for use, e.g., a polyethylene oxide-polypropylene oxide-polyethylene-oxide (PEO-PPO-PEO) triblock co-polymer (e.g., Pluronic® F68); and the like; see, e.g., U.S. Pat. No. 6,923, 986. Other methods for crossing the blood brain barrier are discussed in various publications, including, e.g., Chen et al. (2004) Curr. Drug Delivery 1:361-376.

In some embodiments, a subject functionalized MNP comprises one or more agents that provide for evasion of the reticuloendothelial system (RES). Agents that provide for evasion of the RES include, but are not limited to, a block copolymer non-ionic surfactant such as a poloxamine, such as poloxamine 508, poloxamine 908, poloxamine 1508, etc. For poloxamines, see, e.g., Moghimi and Hunter (2000) *Trends Biotechnol.* 18:412. In some embodiments, a subject functionalized MNP comprises about 1% poloxamine. Poloxamines are polyoxyethylene, polyoxypropylene block copolymers of ethylene diamine.

Nanoparticles can also be transferred across the BBB by utilizing the specific delivery channels that are present in the BBB. As one non-limiting example, attachment of alpha-methyl tryptophan to the nanoparticles renders the tryptophan channels receptive to these particles and aids in delivery across the BBB. Other mechanisms are transcytosis and diapedesis, with or without the mediation of the channels present at the BBB.

Additional Functional Moieties

As noted above, in some embodiments, a subject functionalized MNP will further include at least a second functional moiety.

Suitable at least second functional moieties include, but are not limited to, therapeutic agents; targeting moieties (e.g., moieties that provide for targeting to a particular cell type or tissue type; agents that provide for detection, e.g., dyes; agents that provide for crossing the blood-brain barrier; and the like.

Therapeutic Agents

In some embodiments, the at least second functional moiety is a therapeutic agent, e.g., for delivery to a diseased tissue. Where the disorder is a tumor, suitable therapeutic agents include, but are not limited to, anti-neoplastic agents. Suitable anti-neoplastic agents include those listed above.

Additional Modifications

In some embodiments, the functionalized MNP further comprises an apolipoprotein (e.g., apoA, apoB, or apoE) attached to the functionalized MNP. The apolipoprotein provides for binding to endothelial cells of the BBB, and thus provides for transit of the functionalized MNP across the BBB.

In some embodiments, the functionalized MNP is further processed by attaching human serum albumin and/or apolipoprotein to the functionalized MNP. Human serum albumin (HSA) is attached, covalently or non-covalently (e.g., via ionic interactions) to the functionalized MNP via an acetyl group, via an amino group, via a poly(ethylene glycol) (PEG) linker, or via a thiol bond. Apolipoprotein, or a functional fragment thereof, is attached to the HSA, either covalently or non-covalently. See, e.g. Muller and Keck ((2004) *J. Nanosci. Nanotechnol.* 4:471); and Kreuter et al. ((2002) *J. Drug Target.* 10:317). Amino acid sequences of apolipoproteins are known in the art; for example, amino acid sequences of apoE polypeptides are found at e.g., GenBank Accession Nos. AAD02505; and AAB59397.

In other embodiments, the functionalized MNP further comprises apolipoprotein attached to the functionalized MNP via polysorbate-80. In some embodiments, the functionalized MNP is further processed by attaching polysorbate-80 covalently or non-covalently to the functionalized MNP. In some embodiments, the polysorbate-80 is attached via an acetyl group, via an amino group, via a PEG linker, or via a thiol bond directly to the coating layer. Apolipoprotein is attached to the polysorbate-80, either covalently or non-covalently.

Compositions

The present disclosure further provides compositions, including pharmaceutical compositions, comprising a subject functionalized magnetic nanoparticle. Compositions comprising a subject functionalized magnetic nanoparticle can include one or more of the following: a salt; a buffer; a pH adjusting agent; a non-ionic detergent; a protease inhibitor; a nuclease inhibitor; and the like.

A pharmaceutical composition comprising a subject functionalized MNP will comprise one or more pharmaceutically acceptable carriers. As used herein, "pharmaceutically acceptable carrier" includes any material which, when combined with an active ingredient of a composition, allows the ingredient to retain biological activity and without causing disruptive reactions with the subject's immune system or other physiological function. Examples include, but are not limited to, any of the standard pharmaceutical carriers such as a phosphate buffered saline solution, water, emulsions such as oil/water emulsion, and various types of wetting agents. Exemplary diluents for aerosol or parenteral administration are phosphate buffered saline or normal (0.9%) saline. Compositions comprising such carriers are formulated by well known conventional methods (see, for example, Remington's Pharmaceutical Sciences, Chapter 43, 14th Ed., Mack Publishing Col, Easton Pa. 18042, USA). Pharmaceutically acceptable excipients have been amply described in a variety of publications, including, for example, A. Gennaro (2000) "Remington: The Science and Practice of Pharmacy," 20th edition, Lippincott, Williams, & Wilkins; Remington's Pharmaceutical Sciences, 14th Ed. or latest edition, Mack Publishing Col, Easton Pa. 18042, USA; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

In some embodiments, a subject functionalized MNP is present in a liquid composition at a concentration of from about 1 mg particle weight per ml to about 25 mg particle weight per ml, e.g., from about 1 mg particle weight per ml to about 2 mg particle weight per ml, from about 2 mg particle weight per ml to about 5 mg particle weight per ml, from about 5 mg particle weight per ml to about 7 mg particle weight per ml, from about 7 mg particle weight per ml to about 10 mg particle weight per ml, from about 10 mg particle weight per ml to about 12 mg particle weight per ml, from about 12 mg particle weight per ml to about 15 mg particle weight per ml, from about 15 mg particle weight per ml to about 20 mg particle weight per ml, or from about 20 mg particle weight per ml to about 25 mg particle weight per ml.

A subject functionalized magnetic nanoparticle can be formulated into preparations for injection, for inhalation (e.g., for nasal delivery, for delivery via the respiratory tract), for oral delivery (e.g., oral delivery to the gastrointestinal tract), for delivery through the gastrointestinal tract, for delivery via the genito-urinary tract, for ocular delivery, or for delivery via the skin (e.g., topical delivery via the skin).

In some embodiments, a subject functionalized MNP is suspended in normal saline. In some embodiments, a subject functionalized MNP is suspended in deionized water. In some embodiments, a subject functionalized MNP is suspended in a liquid solution comprising dextrose.

Formulations Suitable for Injection

A subject functionalized magnetic nanoparticle can be formulated into preparations for injection by dissolving, suspending, or emulsifying in an aqueous solvent, or a nonaqueous solvent, such as vegetable or other similar oils, synthetic aliphatic acid glycerides, esters of higher aliphatic acids or propylene glycol. In some embodiments, the formulation will include one or more conventional additives such as solubilizers, isotonic agents, suspending agents, emulsifying agents, stabilizers, and preservatives. Injectable formulations include, but are not limited to, formulations suitable for intravenous injection, formulations suitable for intramuscular injection, formulations suitable for intraocular injection, formulations suitable for peritumoral or intratumoral injection, and formulations for subcutaneous injection.

Formulations Suitable for Delivery Via the Gastrointestinal or Genito-Urinary Tract In some embodiments, a subject functionalized MNP is formulated as a gel, as a solution, a solid, a semi-solid, or in some other form suitable for intravaginal administration. In a further exemplary embodiment, a subject functionalized is formulated as a gel, as a solution, a solid, a semi-solid, or in some other form suitable for rectal (e.g., intrarectal) administration.

A subject functionalized MNP can be formulated for delivery via the genito-urinary tract by formulating the functionalized MNP in a suppository. A subject functionalized can be made into suppositories by mixing with a variety of bases such as emulsifying bases or water-soluble bases. A subject functionalized MNP can be administered rectally via a suppository. The suppository can include vehicles such as cocoa butter, carbowaxes and polyethylene glycols, which melt at body temperature, yet are solidified at room temperature. For suppositories, the composition can include traditional binders and carriers such as, polyalkylene glycols, or triglycerides. Such suppositories may be formed from mixtures containing the active ingredient in the range of about 0.5% to about 10% (w/w), e.g. about 1% to about 2%.

A subject functionalized MNP will in some embodiments be formulated for vaginal delivery. A subject formulation for intravaginal administration can be formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

A subject functionalized MNP will in some embodiments be formulated for rectal delivery. A subject formulation for intrarectal administration is formulated as an intrarectal bioadhesive tablet, intrarectal bioadhesive microparticle, intrarectal cream, intrarectal lotion, intrarectal foam, intrarectal ointment, intrarectal paste, intrarectal solution, or intrarectal gel.

Oral Formulations

In some embodiments, a subject functionalized MNP is formulated for oral delivery. For oral preparations, a subject functionalized MNP can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

For oral delivery, a subject formulation comprising a subject functionalized MNP will in some embodiments include an enteric-soluble coating material. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™, and shellac.

As one non-limiting example of a suitable oral formulation, a subject functionalized MNP is formulated with one or more pharmaceutical excipients and coated with an enteric coating, as described in U.S. Pat. No. 6,346,269. Suitable excipients include pharmaceutically inactive components such as lactose, a starch, mannitol, sodium carboxymethyl cellulose, sodium starch glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin, and castor oil. The formulation can include a stabilizer, where suitable stabilizers include alkali-metals and alkaline earth metals, bases of phosphates and organic acid salts and organic amines. The formulation can also include one or more of talc, stearic acid, stearate, sodium stearyl fumarate, glyceryl behenate, kaolin and aerosil. The formulation can also include one or more of polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalates (CAP), xanthan gum, alginic acid, salts of alginic acid, Eudragit™, copolymer of methyl acrylic acid/methyl methacrylate with polyvinyl acetate phthalate (PVAP). The formulation can also include one or more of glycerin, polyethylene glycol, triethyl citrate, tributyl citrate, propanyl triacetate and castor oil. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™ and shellac.

Suitable oral formulations also include a subject functionalized MNP formulated with any of the following: microgranules (see, e.g., U.S. Pat. No. 6,458,398); biodegradable macromers (see, e.g., U.S. Pat. No. 6,703,037); biodegradable hydrogels (see, e.g., Graham and McNeill (1989) *Biomaterials* 5:27-36); biodegradable particulate vectors (see, e.g., U.S. Pat. No. 5,736,371); bioabsorbable lactone polymers (see, e.g., U.S. Pat. No. 5,631,015); slow release protein polymers (see, e.g., U.S. Pat. No. 6,699,504; Pelias Technologies, Inc.); a poly(lactide-co-glycolide/polyethylene glycol block copolymer (see, e.g., U.S. Pat. No. 6,630,155; Atrix Laboratories, Inc.); a composition comprising a biocompatible polymer and particles of metal cation-stabilized agent dispersed within the polymer (see, e.g., U.S. Pat. No. 6,379,701; Alkermes Controlled Therapeutics, Inc.); and microspheres (see, e.g., U.S. Pat. No. 6,303,148; Octoplus, B.V.).

Suitable oral formulations also include a subject functionalized MNP formulated with any of the following: a carrier such as Emisphere® (Emisphere Technologies, Inc.); TIMERx, a hydrophilic matrix combining xanthan and locust bean gums which, in the presence of dextrose, form a strong binder gel in water (Penwest); Geminex™ (Penwest); Procise™ (GlaxoSmithKline); SAVITT™ (Mistral Pharma Inc.); RingCap™ (Alza Corp.); Smartrix® (Smartrix Technologies, Inc.); SQZgel™ (MacroMed, Inc.); Geomatrix™ (Skye Pharma, Inc.); Oros® Tri-layer (Alza Corporation); and the like.

Also suitable for use herein are formulations comprising a subject functionalized MNP and an intestinal absorption enhancing agent. Suitable intestinal absorption enhancers include, but are not limited to, calcium chelators (e.g., citrate, ethylenediamine tetracetic acid); surfactants (e.g., sodium dodecyl sulfate, bile salts, palmitoylcarnitine, and sodium salts of fatty acids); toxins (e.g., zonula occludens toxin); and the like.

Inhalational Formulations

A subject functionalized MNP will in some embodiments be administered to a patient by means of a pharmaceutical delivery system for the inhalation route. A subject functionalized MNP can be formulated in a form suitable for administration by inhalation. The inhalational route of administration provides the advantage that the inhaled drug can bypass the blood-brain barrier. The pharmaceutical delivery system is one that is suitable for respiratory therapy by delivery of a subject functionalized MNP to mucosal linings of the bronchi. This invention can utilize a system that depends on the power of a compressed gas to expel the functionalized MNP from a container. An aerosol or pressurized package can be employed for this purpose. A subject functionalized MNP can be formulated as a nasal spray.

As used herein, the term "aerosol" is used in its conventional sense as referring to very fine liquid or solid particles carries by a propellant gas under pressure to a site of therapeutic application. When a pharmaceutical aerosol is employed, the aerosol contains a subject functionalized MNP, which can be suspended or emulsified in a mixture of a fluid carrier and a propellant. The aerosol can be in the form of a solution, suspension, emulsion, powder, or semi-solid preparation. Aerosols are intended for administration as fine, solid particles or as liquid mists via the respiratory tract of a patient. Various types of propellants known to one of skill in the art can be utilized. Suitable propellants include, but are not limited to, hydrocarbons such as dichlorodifluoromethane, propane, etc.; nitrogen; and the like. In the case of the pressurized aerosol, the dosage unit may be determined by providing a value to deliver a metered amount.

A subject functionalized MNP can also be formulated for delivery with a nebulizer, which is an instrument that generates very fine liquid particles of substantially uniform size in a gas. For example, a liquid containing a subject functionalized MNP is dispersed as droplets. The small droplets can be carried by a current of air through an outlet tube of the nebulizer. The resulting mist penetrates into the respiratory tract of the patient.

A subject functionalized MNP can be formulated in a powder composition, with or without a lubricant, carrier, or propellant. This embodiment can be used with a conventional device for administering a powder pharmaceutical composition by inhalation. For example, a powder mixture of the functionalized MNP and a suitable powder base such as lactose or starch may be presented in unit dosage form in for example capsular or cartridges, e.g. gelatin, or blister packs, from which the powder may be administered with the aid of an inhaler, with or without a lubricant, carrier, or propellant. This embodiment can be carried out with a conventional device for administering a powder pharmaceutical composition by inhalation. For example, a powder mixture of the functionalized MNP and a suitable powder base such as lactose or starch may be presented in unit dosage form in for example capsular or cartridges, e.g. gelatin, or blister packs, from which the powder may be administered with the aid of an inhaler.

A subject functionalized MNP can be formulated with a low boiling point propellant. Such formulations are generally administered by conventional meter dose inhalers (MDI's). A subject functionalized MNP can be formulated in an aqueous or ethanolic solution and delivered by a conventional nebulizer. A subject functionalized MNP can be formulated into a dry powder formulation. Such a formulation can be administered by simply inhaling the dry powder formulation after creating an aerosol mist of the powder.

Formulations Suitable for Ocular Delivery

A subject functionalized MNP will in some embodiments be formulated for ocular delivery, e.g., where a subject functionalized MNP is formulated for delivery to the eye in liquid form (e.g., eye drops), for injection into or around the eye, etc.

A subject functionalized MNP can be formulated in an ophthalmic pharmaceutical composition. Ophthalmic pharmaceutical compositions can be adapted for topical administration to the eye in the form of solutions, suspensions, ointments, creams or as a solid insert.

For ocular formulations, subject functionalized MNP can be conveniently admixed with a non-toxic pharmaceutical organic carrier, or with a non-toxic pharmaceutical inorganic carrier. Suitable pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethyl-cellulose, polyvinylpyrrolidone, isopropyl myristate and other conventionally employed acceptable carriers. The pharmaceutical preparation can also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitate, dioctyl sodium sulfosuccinate, monothioglycerol, thiosorbitol, ethylenediamine tetracetic acid, and the like.

Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The ocular formulation can also be in the form of a microparticle formulation. The ocular formulation can also be in the form of a solid insert. For example, one may use a solid water soluble polymer as the carrier for the medicament. The polymer used to form the insert can be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyacrylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

A formulation comprising a subject functionalized MNP can further include one or more non-toxic auxiliary substances such as antibacterial components which are non-injurious in use, for example, thimerosal, benzalkonium chloride, methyl and propyl paraben, benzyldodecinium bromide, benzyl alcohol, chlorhexidine, or phenylethanol; buffering ingredients such as sodium borate, sodium acetate, sodium citrate, or gluconate buffers; and other conventional ingredients such as sodium chloride, sorbitan monolaurate, triethanolamine, polyoxyethylene sorbitan monopalmitate, ethylenediaminetetraacetic acid, and the like.

Topical Formulations

A subject functionalized MNP can be formulated for topical administration to the skin. For example, a subject functionalized MNP can be formulated with one or more dermatologically acceptable excipients.

The term "dermatologically acceptable," as used herein, means that the compositions or components thereof so described are suitable for use in contact with human skin without undue toxicity, incompatibility, instability, allergic response, and the like.

In some embodiments, a subject functionalized MNP is formulated with a dermatologically active acid. Suitable dermatologically active acids include a hydroxy acid, ascorbic acid, glycolic acid, magnesium ascorbyl phosphate, sodium ascorbyl phosphate, sodium ascorbate, ascorbyl glucosides, salicylic acid, lipoic acid, dihydrolipoic acid, and combinations thereof. In some embodiments, the dermatologically active acid is alpha-hydroxy acid. Alpha-hydroxy acids include, malic acid, tartaric acid, lactic acid, pyruvic acid, citric acid, and combination of any of the foregoing. In some embodiments, a subject functionalized MNP is formulated with a dermatologically active acid and one or more of: ammonium hydroxide, alkali hydroxide, alkanolamone, amino acid, sodium hydroxide, potassium hydroxide, diethanolamine, triethanolamine, 2-dimethylaminoethanol (dimethyl MEA), aminobutanol, arginine, and lysine.

Suitable excipients include emollients; humectants; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); sugar and starch derivatives (e.g., alkoxylated glucose); hyaluronic acid; lactamide monoethanolamine; acetamide monoethanolamine; and the like.

A variety of emollients can be used. These emollients may be selected from one or more of the following classes: triglyceride esters that include, but are not limited to, vegetable and animal fats and oils such as castor oil, cocoa butter, safflower oil, cottonseed oil, corn oil, olive oil, cod liver oil, almond oil, avocado oil, palm oil, sesame oil, squalene, kikui oil and soybean oil; acetoglyceride esters, such as acetylated monoglycerides; alkyl esters of fatty acids having 10 to 20 carbon atoms which include, but are not limited to, methyl, isopropyl, and butyl esters of fatty acids such as hexyl laurate, isohexyl laurate, isohexyl palmitate, isopropyl palmitate, decyloleate, isodecyl oleate, hexadecyl stearate decyl stearate, isopropyl isostearate, diisopropyl adipate, diisohexyl adipate, dihexyldecyl adipate, diisopropyl sebacate, lauryl lactate, myristyl lactate, and cetyl lactate; alkenyl esters of fatty acids having 10 to 20 carbon atoms such as oleyl myristate, oleyl stearate, and oleyl oleate; fatty acids having 10 to 20 carbon atoms such as pelargonic, lauric, myristic, palmitic, stearic, isostearic, hydroxystearic, oleic, linoleic, ricinoleic, arachidic, behenic, and erucic acids; fatty alcohols having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols; fatty alcohol ethers such as propoxylated fatty alcohols of 10 to 20 carbon atoms which include, but are not limited to, lauryl, cetyl, stearyl, isostearyl, oleyl, and cholesterol alcohols, having attached thereto from 1 to 50 propylene oxide groups; lanolin and lanolin derivatives such as lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated sorbitol lanolin, and liquid and semisolid lanolin absorption bases; polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters; wax esters such as beeswax, spermaceti, myristyl myristate, stearyl stearate; forming a mixture of ether esters; and vegetable waxes including, but not limited to, carnauba and candelilla waxes; and cholesterol fatty acid esters.

Humectants of the polyhydric alcohol-type are suitable for use. Typical polyhydric alcohols include polyalkylene glycols and more preferably alkylene polyols and their derivatives, including propylene glycol, dipropylene glycol, tripropylene glycol, polyethylene glycol and derivatives thereof, sorbitol, hydroxypropyl sorbitol, erythritol, threitol, pentaerythritol, xylitol, glucitol, mannitol, hexylene glycol, 1,3-butylene glycol, 1,2,6-hexanetriol, glycerol, ethoxylated glycerol, propoxylated glycerol, sodium 2-pyrrolidone-5-carboxylate, soluble collagen, gelatin and mixtures thereof.

Also useful herein are guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); sugar and starch derivatives (e.g., alkoxylated glucose); hyaluronic acid; lactamide monoethanolamine; acetamide monoethanolamine; and mixtures thereof.

A composition comprising a subject functionalized MNP can include a dermatologically-acceptable hydrophilic diluent. Non-limiting examples of hydrophilic diluents are water, organic hydrophilic diluents such as lower monovalent alcohols (e.g., $C_1$-$C_4$ alcohols) and low molecular weight glycols and polyols, including propylene glycol, polyethylene glycol (e.g., Molecular Weight 200-600 g/mole), polypropylene glycol (e.g., Molecular Weight 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof. A composition comprising a subject functionalized MNP can contain from about 60% to about 99.99% of a hydrophilic diluent.

A composition comprising a subject functionalized MNP can include a dermatologically acceptable carrier. An example of a suitable carrier is an emulsion comprising a hydrophilic phase comprising a hydrophilic component, e.g., water or other hydrophilic diluent, and a hydrophobic phase comprising a hydrophobic component, e.g., a lipid, oil or oily material. The hydrophilic phase will be dispersed in the hydrophobic phase, or vice versa, to form respectively hydrophilic or hydrophobic dispersed and continuous phases, depending on the composition ingredients. In emulsion technology, the term "dispersed phase" is a term well known to one skilled in the art which means that the phase exists as small particles or droplets that are suspended in and surrounded by a continuous phase. The dispersed phase is also known as the internal or discontinuous phase. The emulsion may be or comprise (e.g., in a triple or other multi-phase emulsion) an oil-in-water emulsion or a water-in-oil emulsion such as a water-in-silicone emulsion. Oil-in-water emulsions can comprise from about 1% to about 50% of the dispersed hydrophobic phase and from about 1% to about 98% of the continuous hydrophilic phase; water-in-oil emulsions can comprise from about 1% to about 98% of the dispersed hydrophilic phase and from about 1% to about 50% of the continuous hydrophobic phase.

A subject functionalized MNP can be formulated with common excipients, diluents, or carriers, and formed into lotions, creams, solutions, suspensions, powders, aerosols, emulsions, salves, ointments and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinylpyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The topical formulation can include thickening agents such as cellulose and/or cellulose derivatives. The topical formulation can include contain gums such as xanthan, guar or carbo gum or gum arabic, or alternatively poly(ethylene glycol)s, bentones and montmorillonites, and the like.

Screening Methods

The present disclosure provides drug discovery and design methods, e.g., screening methods, or methods of identifying an agent that binds a cell surface receptor and elicits at least one biological activity in a cell expressing the receptor on its surface. The methods generally involve conjugating an agent to an MNP, forming an agent-MNP conjugate; contacting the agent-MNP conjugate with a eukaryotic cell that expresses on its cell surface a receptor for the agent; and determining (e.g., assaying) the effect, if any, of the agent-MNP conjugate on at least one biological activity of the cell. A subject drug discovery method can reduce the cost and/or time to identify and/or design active agents.

In some embodiments, the contacting step is carried out in vitro. In some embodiments, the cell is a primary cell. In some embodiments, the cell is a cell line, e.g., an immortalized cell line. In some embodiments, the cell is a genetically modified cell that is genetically modified with a nucleic acid that comprises a nucleotide sequence encoding a receptor for the agent.

In some embodiments, the agent is a peptide. The peptide can be conjugated to the MNP, directly or via a linker. The peptide can be conjugated to a biocompatible substrate surrounding or attached to an MNP, where the peptide is conjugated to the biocompatible substrate directly or via a linker.

The effect, if any, of the agent-MNP conjugate on a biological activity of a cell can be determined (assayed) using any known assay that measures the biological activity. Biological activities that can be measured include, but are not limited to, production of cyclic AMP, production of a cytokine, a change in intracellular potassium concentration, a change in intracellular calcium concentration, a change in intracellular sodium concentration, a voltage change, expression of one or more mRNA and/or proteins that reflect a differentiation state, apoptosis, etc.

In some embodiments, the agent being tested is a polypeptide agent. Polypeptide agents can have a length of from about 5 amino acids to about 25 amino acids, from about 25 amino acids to about 50 amino acids, from about 50 amino acids to about 100 amino acids, from about 100 amino acids to about 500 amino acids, or longer than 500 amino acids. In some embodiments, a polypeptide agent is attached to the MNP, directly or via a linker. In some embodiments, a polypeptide agent is attached to a biocompatible substrate that surrounds or is attached to the MNP, where the polypeptide agent is attached to the biocompatible substrate directly or via a linker. Methods for attaching a polypeptide agent to an MNP or to a biocompatible substrate attached to or surrounding a magnetic nanoparticle are known in the art. In some embodiments, a polypeptide agent is attached via the carboxyl-terminal COOH group of the polypeptide agent. In some embodiments, a polypeptide agent is attached via the amino-terminal $NH_3$ group of the polypeptide agent. In other embodiments, a polypeptide agent via an amino acid side chain of an internal amino acid, a carboxyl-terminal amino acid, or an amino-terminal amino acid, of the polypeptide agent. Amino acid side chains that are suitable for linkage include, but are not limited to, lysine (e.g., epsilon amino group of lysine), cysteine (e.g., sulfhydryl group of cysteine), etc.

In some embodiments, conjugation of a polypeptide agent to an MNP increases the potency of the polypeptide agent. In some embodiments, conjugation of a polypeptide agent to an MNP increases the efficacy of the polypeptide agent. In some embodiments, conjugation of a polypeptide agent to an MNP decreases the potency and increases the efficacy of the polypeptide agent. For example, in some embodiments, conjugation of a polypeptide agent to an MNP increases the efficacy of the polypeptide agent, e.g., the efficacy in stimulating at least one biological activity in a target cell, by at least about 5%, at least about 10%, at least about 25%, at least about 50%, at least about 100% (or 2-fold), at least about 2.5-fold, at least about 5-fold, at least about 10-fold, or more than 10-fold, compared with the efficacy of unconjugated polypeptide agent.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. In some embodiments, the cell line exemplifies a particular mammalian (e.g., human) cancer.

In some embodiments, the cell is a neuronal cell or a neuronal-like cell. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

In some embodiments, a subject method for identifying an active agent further comprises testing whether the active agent is cytotoxic. For example, in some embodiments, an agent-MNP conjugate is assessed for any cytotoxic activity it may exhibit toward a living eukaryotic cell, using well-known assays, such as trypan blue dye exclusion, an MTT (3-(4,5-dimethylthiazol-2-yl)-2,5-diphenyl-2H-tetrazolium bromide) assay, and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Imaging 2DG MNPs in an Animal Model of Intracranial Tumors

2DG-functionalized MNPs were applied to an animal model of intracranial tumors. MRI scans were acquired. Uptake of 2DG-functionalized MNPs by intracranial tumors was shown; the 2DG-functionalized MNPs were able to clearly delineate tumor tissues from the surrounding normal (non-cancerous) brain tissues.

Methods

Tumor studies—

Nude mice were injected intracranially with glioblastoma cell line U87Rluc (U87 glioblastoma cell line (ATCC HTB14) genetically modified to express luciferase). Dextran-coated magnetic nanoparticles were functionalized with 2DG. The 2DG moiety was attached to the dextran via the 6-carbon of 2DG. Baseline MR scans were obtained prior to injection with 2DG-MNP. Immediately after baseline scans, the mice were injected with 2DG-MNP (7 mg particles/kg body weight; 1.7 mg Fe/kg body weight) through the tail vein. Scans were obtained at 2 hours, 6 hours, and 24 hours post-MNP injection.

Results

The results are shown in FIGS. 1A-D, and FIGS. 2A-D.

FIG. 1a shows the MRI of a mouse with a glioblastoma prior to i.v. 2DG-MNP injection. FIGS. 1b-d show negative contrast enhancement in the glioblastoma at 2 hours, 6 hours, and 24 hours after i.v. injection of 2DG-MNP. Clearing is seen at 24 hours. Negative enhancement due to particle uptake as well as tumor delineation is clearly visible.

FIG. 2a shows MRI images in the resting mouse brain before i.v. 2DG-MNP injection, and FIGS. 2b-d show images obtained two hours, six hours, and 24 hours after i.v. injection of 2DG-MNP. Uniform uptake, displayed as negative enhancement, is observed especially in the thalamus and neocortex. Contrast cleared slowly over 24 hours.

Example 2

Comparison of 2DG-MNP Imaging and Gadolinium Imaging

Brains of mice with medulloblastoma were imaged. Magnetic resonance (MR) images were obtained with multiple slice multiple echo (MSME) T2 scan (TR=6000 ms, TE 10-60 ms in steps of 10 ms, FOV=35 mm, slice thickness=1 mm, zero spacing) on a 7T magnet (Broker Biospin, Germany). Mice were administered with: 1) no contrast agent; 2) gadolinium; or 3) 2DG-MNP.

Figure 3A:
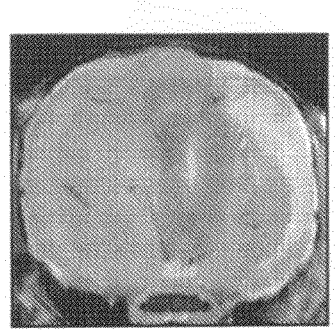
FIGS. 3A and 3B depict: 3A) a baseline image of the mouse brain with a large medulloblastoma; and 3B) a T2 reconstruction of the image in 3A.
Figure 3B:
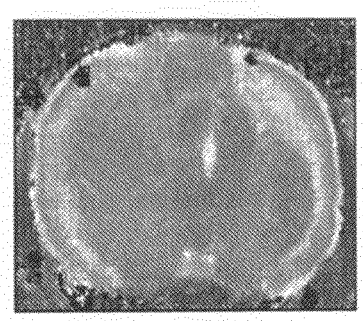

FIGS. 3A and 3B show brain images from mice administered no contrast agent. FIG. 3A shows the baseline image of the mouse brain with a large medulloblastoma. FIG. 3B shows the T2 reconstruction of the image in FIG. 3A. The T2 value of the tumor was measured at 57.7±2.3 ms.

Figure 4A:
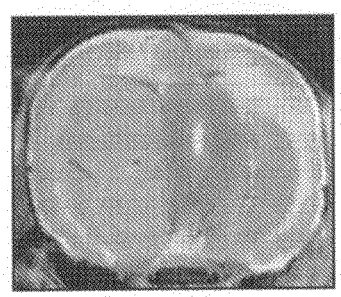
FIGS. 4A and 4B depict: 4A) a magnetic resonance imaging (MRI) scan of the mouse brain with a large medulloblastoma, after injection of 100 µl of gadonlinium chelate; and 4B) a T2 reconstruction of the image in 4A.
Figure 4B:
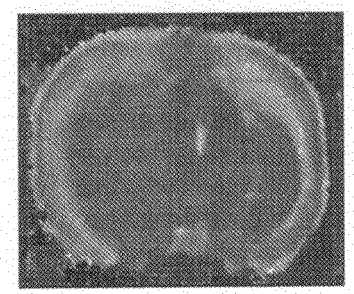

FIGS. 4A and 4B show brain images from mice administered with gadolinium. FIG. 4A shows the MRI scan of the same mouse after injection with 100 μl of Gadolinium chelate (Gado). FIG. 4B shows the T2 reconstruction of the image in FIG. 4A. The T2 value of the tumor was measured at 51.3±2.1 ms.

Figure 5A:
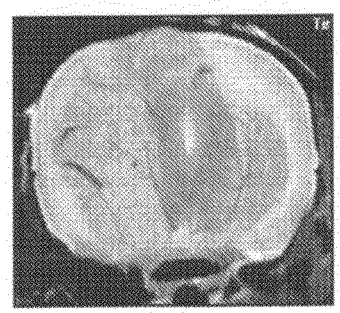
FIGS. 5A and 5B depict: 5A) an MRI scan of the mouse brain with a large medulloblastoma, after injection with 100 µl of 2DG-MNP; and 5B) a T2 reconstruction of the image in 5A.
Figure 5B:
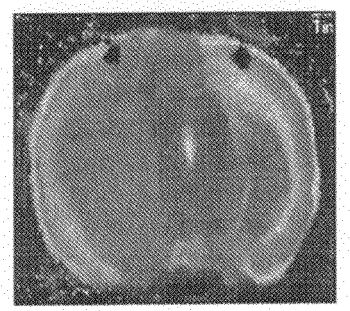

FIGS. 5A and 5B brain images from mice administered with 2DG-MNP. FIG. 5A shows the MRI scan of the same mouse after injection with 100 μl of 2DG-MNP. FIG. 5B shows the T2 reconstruction of the image in FIG. 5A. The T2 value of the tumor was measured at 48.2±2.5 ins.

These data show that 2DG-MNP decreases tissue T2 values more that Gado, and that 2DG-MNP reveal more tumor tissue that Gado (gadolinium). Furthermore, 2DG-MNP can be used to stage and grade tumors pre- and post-treatment, whereas Gado has limited utility for such applications.

Example 3

Adrenocorticotropin Hormone (ACTH) Conjugated Magnetonanoparticles for Visualization of Adrenal Gland and its Diseases using MRI This example relates to Adrenocorticotropin Hormone (ACTH) conjugated to magnetonanoparticles. ACTH-functionalized MNPs can visualize diseases of adrenal gland such as adrenal dysplasia or tumors in utero and its development throughout life or after regeneration or transplant in MRI. MNP's that can also pass the BBB are attached to receptor (and their subtypes) ligands such as ACTH and its derivatives or variants or other hormones or factors and their derivatives or variants. The diseased tissue such as the adrenal gland has increased or decreased tissue and/or number of receptor sites (and/or their variants and/or their subtypes) for ACTH leading to increased (or decreased) number of MNP-ACTH attachment to the tissue. In the case of lower number of receptor sites, fewer of these particles attach to neoplastic, or other central or systemic diseases and disorders than normal tissues. In the case of higher affinity, more of these particles attach to the diseased tissues than normal brain tissues. This differential attachment will lead to decreasing T2, T2*, and T1 time of the protons leading to a loss of "signal" in the vicinity of tissues with higher MNP concentration.

Adrenocorticotropin Hormone (ACTH)-conjugated dextran-coated and epoxy surface-modified magnetonanoparticles (MNP's, 10-15 nm diameter) were synthesized. These ACTH-MNPs were designed to pass the placenta and blood brain barrier (BBB) if necessary. ACTH was conjugated via its nitrogen atoms to magnetonanoparticles via C3-epoxy linkers or directly to the coating of the nanoparticle. The magnetonanoparticle can also be attached via linker or directly to any of the atoms residing in the ACTH polypeptide or other hormones and their variants or derivatives. Differential distribution of these particles in diseased and non-diseased tissues provides contrast in MRI. These particles have also a relatively long tissue half-life (order of hours to days), which makes it feasible to monitor development and progression of tissue changes through time without the need for renewed administration of these agents. The compounds also have long shelf-life (2-3 months) which makes them available for use where MR scanners are available without the need for real time synthesis as is needed with positron emission tomography (PET).

Materials and Methods

ACTH was conjugated at $NH^+_3$ group of Lysine to dextran coated and epoxy-surface modified magnetonanoparticles of approximately 10 nm in diameter. The synthetic scheme is shown below.

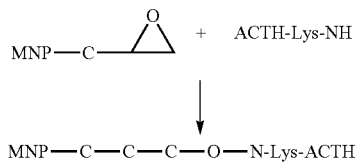

ACTH-MNP was injected through tail vein (approximately 1 µg iron-oxide per gram of body weight) in a 1-day old mouse and a 60-day old mouse. MR images (T2, TE 6000, TR=$10^{-10}$ ms, 0.4-1 mm slice thickness, 3 cm FOV, Brucker Biospin 7T) were obtain before, and up to 3 hours after injection with these contrast agents.

Results

Figure 6C:
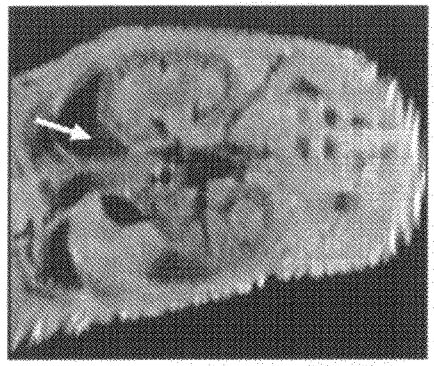
FIGS. 6A-E depict: the no-contrast MR image of the right adrenal gland in a 1-day old mouse (FIG. 6A); the right and left adrenal glands (FIGS. 6B and 6C, respectively) after injection with 5 µl of ACTH-MNP contrast agent; MR images of adrenal glands before (FIG. 6D) and after (FIG. 6E) injection of 100 µl of ACTH-MNP contrast agents in a 60 day old mouse.
Figure 6B:
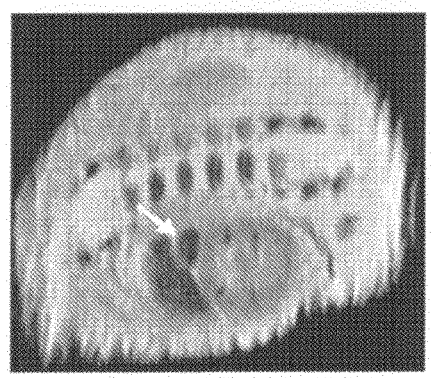
Figure 6E:
Figure 6A:
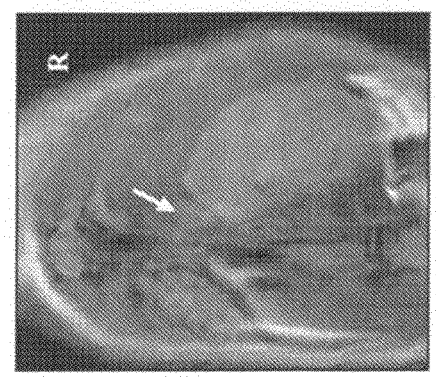
Figure 6D:
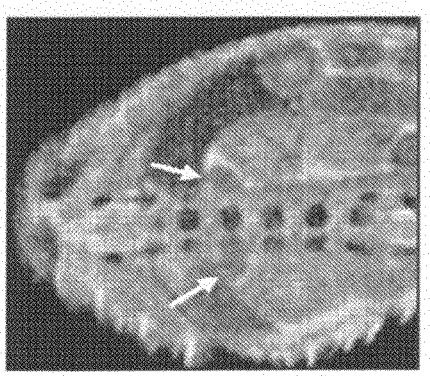

FIG. 6A shows the no-contrast MR image of the right adrenal gland in a 1-day old mouse. FIGS. 6B and 6C show the right and left adrenal glands, respectively, after injection with 5 µl of ACTH-MNP contrast agent. The results show increased uptake (decreased signal intensity) in the adrenals. FIGS. 6D and 6E show the MR images of adrenal glands before and after injection of 100 µl of ACTH-MNP contrast agents in a 60 day old mouse. The results show increased uptake (decreased signal intensity) in the adrenals. The differences in enhancement between the two mice represent different stages of adrenal development during the life cycle of the animals.

Example 4

Corticotropin Releasing Hormone (CRF) Conjugated Magnetonanoparticles for Visualization of Neoplasm (e.g., Pituitary Tumors) on MRI This example relates to corticotropin releasing factor (CRF) (or hormone) conjugated to magnetonanoparticles (MNPs). This combination can also visualize pituitary tumors in particular in MRI. Pituitary tumors have increased receptors for CRF compared with normal pituitary tissues.

The diseased tissue such as the pituitary tumor has increased number of receptor sites (and/or their variants and/or their subtypes) for CRF leading to increased number of MNP-CRF attachment to the tissue. In the case of lower number of receptor sites, fewer of these particles attach to neoplastic tissues, or tissues associated with other central or systemic diseases and disorders, compared to normal tissues. In the case of higher affinity, more of these particles attach to the diseased tissues than normal brain tissues. This differential attachment will lead to decreasing T2, T2*, and T1 time of the protons leading to a loss of "signal" in the vicinity of tissues with higher MNP concentration.

CRF-conjugated dextran-coated and maleimide surface-modified magnetonanoparticles (MNP's, 10-15 nm diameter) were synthesized. These CRF-MNPs were designed to pass the blood brain barrier (BBB) if necessary. CRF was conjugated via its sulfur atoms to magnetonanoparticles via maleimide linkers or directly to the coating of the nanoparticle. The magnetonanoparticle can also be attached via linker or directly to any of the atoms residing in the CRF polypeptide or other hormones and their variants or derivatives. Differential distribution of these particles in diseased and non-diseased tissues provides contrast in MRI. These particles have also a relatively long tissue half-life (order of hours to days), which makes it feasible to monitor development and progression of tissue changes through time without the need for renewed administration of these agents. The compounds also have long shelf-life (6-12 months) which makes them available for use where MR scanners are available without the need for real time synthesis as is needed with positron emission tomography (PET).

Materials and Methods

Particles: CRF was conjugated to dextran coated and maleimide-surface modified magnetonanoparticles of a diameter of approximately 10 nm in diameter. The synthetic scheme is shown below.

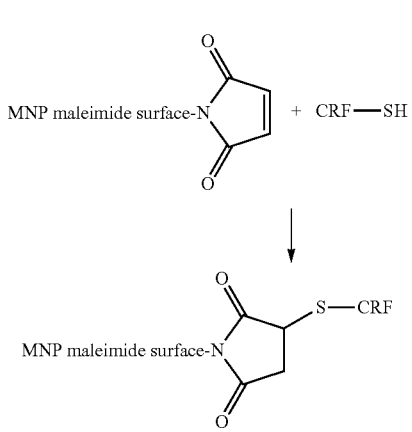

Functional studies of tumor cells. Murine pituitary tumor cell lines (AtT-20 cells; American Type Culture Collection designation CCL-89™) were incubated with CRF and CRF-MNP preparations at 6 different molar concentrations of CRF and CRF-equivalent concentration of CRF-MNP ($10^{-12}$-$10^{-7}$ molar, factor of 10 increase per step). Production of c-AMP (nM) was measured after equivalent times of incubation with all the preparations.

Results

Figure 7:
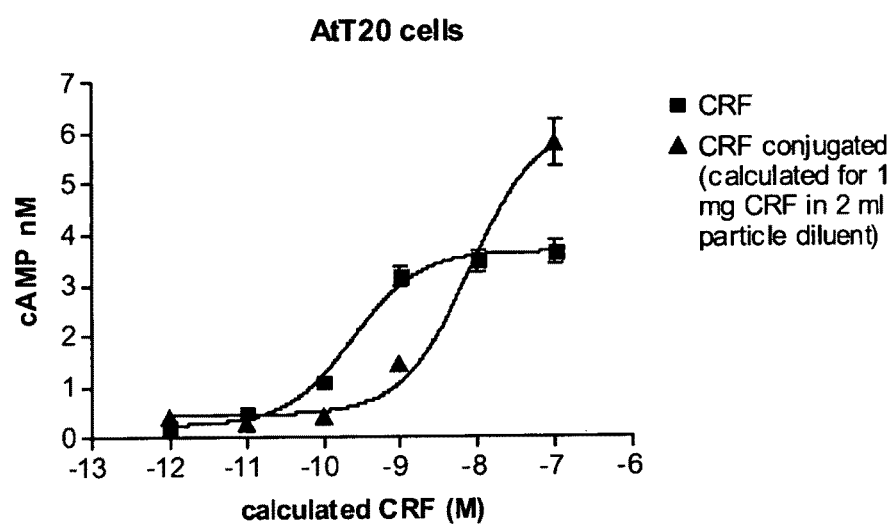
FIG. 7 depicts functional activity of CRF-MNP compared to CRF at equivalent CRF concentrations.

FIG. 7 shows the functional activity of CRF-MNP compared CRF at equivalent CRF concentrations. The results show an approximately 10-fold decrease in potency and two-fold increase in efficacy. These results also show: 1) CRF retains its functional properties at the cellular level while conjugated to the nanoparticles, 2) the CRF-MNP compound is not cytotoxic.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of detecting a cancer cell in an individual, the method comprising
   a) administering to the individual a pharmaceutical composition comprising:
      i) a functionalized magnetic nanoparticle (MNP) of the formula M-S-(L)-Z, wherein M is a magnetic core, S is a polymer, L is an optional linker, and Z is a functional moiety that has differential affinity for and/or metabolic uptake into a cancer cell,
      wherein the functional moiety is corticotropin releasing hormone, and wherein the cancer cell is a pituitary tumor cell;
      wherein the functional moiety is adrenocorticotropin hormone, and wherein the cancer cell is an adrenal dysplasia or tumor; or
      wherein the functional moiety is 2-deoxyglucose (2DG) and wherein the 2DG is linked via the 6-OH group of the 2DG; and
      ii) a pharmaceutically acceptable carrier; and
   b) detecting the functionalized MNP in association with the cancer cell.

2. The method of claim 1, wherein the functionalized MNP further comprises at least a second functional moiety.

3. The method of claim 2, wherein the second functional moiety comprises a cancer chemotherapeutic agent.

4. The method of claim 1, wherein said detecting comprises magnetic resonance imaging.

5. The method of claim 1, wherein said detecting comprises computed tomography.

6. A method of grading a cancer, the method comprising:
   a) administering to an individual having or suspected of having a cancer a pharmaceutical composition comprising:
      i) a functionalized magnetic nanoparticle (MNP) of the formula M-S-(L)-Z, wherein M is a magnetic core, S is a polymer, L is an optional linker, and Z is a functional moiety that has differential affinity for and/or metabolic uptake into a cancer cell,
      wherein the functional moiety is corticotropin releasing hormone, and wherein the cancer cell is a pituitary tumor cell;
      wherein the functional moiety is adrenocorticotropin hormone, and wherein the cancer cell is an adrenal dysplasia or tumor; or
      wherein the functional moiety is 2-deoxyglucose (2DG) and wherein the 2DG is linked via the 6-OH group of the 2DG; and
      ii) a pharmaceutically acceptable carrier; and
   b) detecting the level of the functionalized MNP in association with a tissue containing a cancer cell, wherein a level of functionalized MNP correlates with a grade of cancer.

7. A method of treating a cancer in an individual, the method comprising administering to the individual a pharmaceutical composition comprising:
   i) a functionalized magnetic nanoparticle (MNP) of the formula M-S-(L)-$Z_1Z_2$, wherein M is a magnetic core particle, S is a polymer, L is an optional linker, $Z_1$ is a first functional moiety that has differential affinity for and/or metabolic uptake into a cancer cell, and $Z_2$ is a second functional moiety that is a cancer chemotherapeutic agent, wherein $Z_1$ is corticotropin releasing hormone, and wherein the cancer cell is a pituitary tumor cell;

wherein $Z_1$ is adrenocorticotropin hormone, and wherein the cancer cell is an adrenal dysplasia or tumor; or wherein $Z_1$ is 2-deoxyglucose (2DG) and wherein the 2DG is linked via the 6-OH group of the 2DG; and ii) a pharmaceutically acceptable carrier;

wherein the functionalized MNP associates with a cancer cell in the individual, and wherein the cancer chemotherapeutic agent treats the cancer.

8. The method of claim 7, wherein the cancer chemotherapeutic agent is an alkylating agent, a nitrosourea, an antimetabolite, an antitumor antibiotic, a plant (vinca) alkaloid, or a steroid hormone.

9. A method of treating a cancer in an individual, the method comprising:
  a) administering to the individual a pharmaceutical composition comprising:
    i) a functionalized magnetic nanoparticle (MNP) of the formula M-S-(L)-Z, wherein M is a magnetic core, S is a polymer, L is an optional linker, and Z is a functional moiety that has differential affinity for and/or metabolic uptake into a cancer cell,
  wherein the functional moiety is corticotropin releasing hormone, and wherein the cancer cell is a pituitary tumor cell;
  wherein the functional moiety is adrenocorticotropin hormone, and wherein the cancer cell is an adrenal dysplasia or tumor; or
  wherein the functional moiety is 2-deoxyglucose (2DG) and wherein the 2DG is linked via the 6-OH group of the 2DG; and
    ii) a pharmaceutically acceptable carrier;
  b) detecting the presence of the functionalized MNP in association with the cancerous tissue; and
  c) carrying out a cancer therapy regimen on the individual.

10. The method of claim 9, wherein the cancer therapy regimen comprises surgical removal of the cancer, radiation therapy, cancer chemotherapy, bone marrow transplantation, or hyperthermic ablation.

11. The method of claim 1, wherein the polymer is dextran.

12. The method of claim 1, wherein the functional moiety is corticotropin releasing hormone, and wherein the cancer cell is a pituitary tumor cell.

13. The method of claim 1, wherein the functional moiety is adrenocorticotropin hormone, and wherein the cancer cell is an adrenal dysplasia or tumor.

14. The method of claim 1, wherein the functional moiety is 2-deoxyglucose (2DG), and wherein the 2DG is linked via the 6-OH group of the 2DG.

15. The method of claim 14, wherein the 2DG is directly attached to the polymer via the 6-OH group of the 2DG.

16. The method of claim 6, wherein the polymer is dextran.

17. The method of claim 6, wherein the functional moiety is 2DG, and wherein the 2DG is attached to the polymer via the 6-OH group of the 2DG.

18. The method of claim 7, wherein the polymer is dextran.

19. The method of claim 7, wherein the functional moiety is 2DG, and wherein the 2-deoxyglucose is attached to the polymer via the 6-OH group of the 2DG.

20. The method of claim 9, wherein the polymer is dextran.

21. The method of claim 9, wherein the functional moiety is 2DG, and wherein the 2DG is attached to the polymer via the 6-OH group of the 2DG.

* * * * *